(12) United States Patent
Meng

(10) Patent No.: US 10,544,142 B2
(45) Date of Patent: Jan. 28, 2020

(54) CRYSTAL FORMS OF PALBOCICLIB, AND PREPARATION METHOD AND USE THEREFOR

(71) Applicant: SHANGHAI BEGREAT PHARMATECH, Shanghai (CN)

(72) Inventor: Xiaoming Meng, Tianjin (CN)

(73) Assignee: SHANGHAI BEGREAT PHARMATECH, Shanghai (CN)

( * ) Notice: Subject to any disclaimer, the term of this patent is extended or adjusted under 35 U.S.C. 154(b) by 0 days.

(21) Appl. No.: 16/184,009

(22) Filed: Nov. 8, 2018

(65) Prior Publication Data

US 2019/0071442 A1    Mar. 7, 2019

Related U.S. Application Data

(63) Continuation of application No. PCT/CN2017/000339, filed on May 8, 2017.

(30) Foreign Application Priority Data

May 8, 2016  (CN) .......................... 2016 1 0300156

(51) Int. Cl.
*A61K 31/519* (2006.01)
*C07D 471/04* (2006.01)

(52) U.S. Cl.
CPC ........ *C07D 471/04* (2013.01); *C07B 2200/13* (2013.01)

(58) Field of Classification Search
CPC ........................... A61K 31/519; C07D 471/04
USPC ...................................... 514/264.11; 544/279
See application file for complete search history.

(56) References Cited

U.S. PATENT DOCUMENTS

2016/0002223 A1    1/2016 Chekal et al.

FOREIGN PATENT DOCUMENTS

CN           105418603 A      3/2016

OTHER PUBLICATIONS

International Search Report in PCT/CN2017/000339 dated Nov. 2, 2017, 3 pages.

*Primary Examiner* — Jeffrey H Murray
(74) *Attorney, Agent, or Firm* — Metis IP LLC

(57) ABSTRACT

A plurality of new crystal Forms I, II, III, IV, V, VI, VII, VIII, IX, X, XI, XII and XIV of 6-Acetyl-8-cyclopentyl-5-methyl-2-(5-piperazin-1-yl-pyridin-2-ylamino)-8H-pyrido[2,3-d]pyrimidin-7-one, as well as a preparation method and medicinal use therefor are disclosed in the present disclosure. Crystal Form VIII is a semi-hydrate crystal Form. Compared to crystal Forms of the prior art, these new crystal Forms are markedly superior in respect of dissolution, stability, and the preparation process.

4 Claims, 35 Drawing Sheets

CRYSTAL FORMS OF PALBOCICLIB, AND PREPARATION METHOD AND USE THEREFOR

CROSS-REFERENCE TO RELATED APPLICATIONS

This application is a continuation of International Application No. PCT/CN2017/000339, filed on May 8, 2017, which claims priority of Chinese Application No. 201610300156.0, filed on May 8, 2016, the contents of each of which are hereby incorporated by reference.

TECHNICAL FIELD

The present disclosure relates to novel crystals of 6-Acetyl-8-cyclopentyl-5-methyl-2-(5-piperazin-1-yl-pyridin-2-ylamino)-8H-pyrido[2,3-d]pyrimidin-7-one and its preparation method and use.

BACKGROUND

Compound 1, Palbociclib (6-acetyl-8-cyclopentyl-5-methyl-2-(5-piperazin-1-yl-pyridin-2-ylamino)-8H-Pyrido [2,3-d]pyrimidin-7-one) is a drug approved by the US FDA and is an oral inhibitor of cyclin-dependent kinase 4, 6 (CDK4/6). There is a precise program named cell cycle regulation mechanism that regulates cell growth, proliferation, or death in every living individual. The disruption of cell cycle regulation mechanisms leads to uncontrolled growth of cells, a common feature of almost all tumor development. In the mammalian cell cycle, the regulation point from the G1 phase to the S phase, the R point (Restriction point), is a key point in the regulation of cell proliferation. Only the breakthrough of the R point, DNA replication in S phase can be triggered for cell proliferation. The regulation of this point is closely related to the occurrence and development of tumors. Palbociclib can target the G1 phase of the cell cycle and block the proliferation of cancer cells. Palbociclib is used in patients with advanced breast cancer who are estrogen receptor (ER) positive, human epidermal growth factor receptor-2 (HER2) negative, and postmenopausal women.

Palbociclib has a molecular Formula of $C_{24}H_{29}N_7O_2$ and a molecular weight of 447.53. The chemical structure of Palbociclib (Compound 1) is as follows:

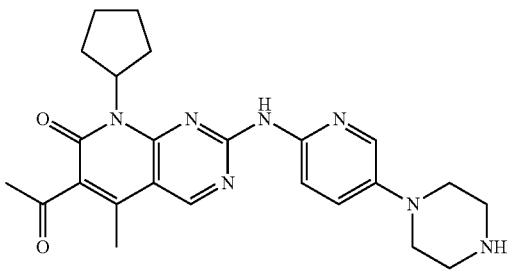 [SMILES: CC(=O)c1c(C)c2cnc(Nc3ccc(N4CCNCC4)cn3)nc2n(C2CCCC2)c1=O]

Chemical raw materials of active pharmaceutical ingredients (API) must have good purity, stability, physical and chemical properties and operability. These properties are related to the crystalline Form of the drug, and different crystal Forms have different physical and chemical properties. The purpose of improving the stability of the drug preservation and the efficacy of the drug, it is necessary to make the raw API into crystal Form.

A drug may exist in a plurality of crystalline Forms, and different crystal Forms of the same drug may have different dissolution and absorption in the body, thereby affecting the dissolution and release of the Formulation.

The optimal crystalline Form can be discovered by thoroughly studying of the polymorphism of the compound. The optimal crystalline Form is crucial to the efficacy of the drug and the Formulation process which is based on the characteristics of the crystalline Form, thereby effectively ensuring the equivalence of the drug batch to batch.

However, in the prior art, the solubility of Palbociclib in crystal Forms A and B in water is very small, which is detrimental to the dissolution and release of the drug, resulting in a decrease in bioavailability and a food effect.

SUMMARY

The present disclosure relates to novel crystals of 6-Acetyl-8-cyclopentyl-5-methyl-2-(5-piperazin-1-yl-pyridin-2-ylamino)-8H-pyrido[2,3-d]pyrimidin-7-one and its preparation method and use.

Some embodiments of the present disclosure provide the crystal Form I of 6-Acetyl-8-cyclopentyl-5-methyl-2-(5-piperazin-1-yl-pyridin-2-ylamino)-8H-pyrido[2,3-d]pyrimidin-7-one which can be characterized by X-ray powder diffraction (XRPD) patterns including diffraction peaks, measured using CuKα radiation, at at least one 2θ value of 19.1±0.2, 10.7±0.2, 21.7±0.2, 19.7±0.2, or 9.5±0.2. In some embodiments, the X-ray powder diffraction pattern further includes diffraction peaks, measured using CuKα radiation, at 2θ values of 5.6±0.2, 22.1±0.2, 22.4±0.2, 13.1±0.2, 10.1±0.2, 16.6±0.2, and 28.5±0.2. In some embodiments, the X-ray powder diffraction pattern further includes diffraction peaks, measured using CuKα radiation, at 2θ values of 23.8±0.2, 17.0±0.2, 7.8±0.2, 12.6±0.2, 26.3±0.2, 22.9±0.2, 11.4±0.2, and 28.8±0.2.

Some embodiments of the present disclosure provide the crystal Form II of 6-Acetyl-8-cyclopentyl-5-methyl-2-(5-piperazin-1-yl-pyridin-2-ylamino)-8H-pyrido[2,3-d]pyrimidin-7-one which can be characterized by XRPD patterns including diffraction peaks, measured using CuKα radiation, at at least one 2θ value of 19.2±0.2, 9.6±0.2, 11.4±0.2, 22.5±0.2, or 12.1±0.2. In some embodiments, the X-ray powder diffraction pattern further includes diffraction peaks, measured using CuKα radiation, at 2θ values of 5.6±0.2, 22.1±0.2, 22.4±0.2, 13.1±0.2, 10.1±0.2, 16.6±0.2, 28.5±0.2, 16.7±0.2, 21.7±0.2, 7.6±0.2, 8.9±0.2, 13.0±0.2, and 15.3±0.2. In some embodiments, the X-ray powder diffraction pattern further includes diffraction peaks, measured using CuKα radiation, at 2θ values of 17.3±0.2, 19.7±0.2, 23.8±0.2, 27.2±0.2, 16.3±0.2, 26.5±0.2, 28.4±0.2 and 14.4±0.2.

Some embodiments of the present disclosure provide the crystal Form III of 6-Acetyl-8-cyclopentyl-5-methyl-2-(5-piperazin-1-yl-pyridin-2-ylamino)-8H-pyrido[2,3-d]pyrimidin-7-one which can be characterized by XRPD patterns including diffraction peaks, measured using CuKα radiation, at at least one 2θ value of 8.4±0.2, 24.3±0.2, 26.6±0.2, 12.9±0.2, or 9.6±0.2. In some embodiments, the X-ray powder diffraction pattern further includes diffraction peaks, measured using CuKα radiation, at 2θ values of 16.3±0.2, 6.4±0.2, 25.6±0.2, 10.1±0.2, 21.7±0.2. In some embodiments, the X-ray powder diffraction pattern further includes diffraction peaks, measured using CuKα radiation, at 2θ values of 27.7±0.2, 12.1±0.2, 15.7±0.2, 21.4±0.2, 22.4±0.2, 18.4±0.2, and 18.8±0.2.

Some embodiments of the present disclosure provide the crystal Form IV of 6-Acetyl-8-cyclopentyl-5-methyl-2-(5-piperazin-1-yl-pyridin-2-ylamino)-8H-pyrido[2,3-d]pyrimidin-7-one which can be characterized by XRPD patterns including diffraction peaks, measured using CuKα radiation, at at least one 2θ value of 11.1±0.2, 24.3±0.2, 21.7±0.2, 18.7±0.2, or 18.2±0.2. In some embodiments, the X-ray powder diffraction pattern further includes diffraction peaks, measured using CuKα radiation, at 2θ values of 12.4±0.2, 15.7±0.2, 14.6±0.2, 25.3±0.2, and 22.1±0.2. In some embodiments, the X-ray powder diffraction pattern further includes diffraction peaks, measured using CuKα radiation, at 2θ values of 20.4±0.2, 27.2±0.2, 7.9±0.2, 7.3±0.2, 17.0±0.2, 9.8±0.2, 13.4±0.2, 13.9±0.2, 30.1±0.2, 32.6±0.2, 23.0±0.2, 9.2±0.2, and 26.1±0.2.

Some embodiments of the present disclosure provide the crystal Form V of 6-Acetyl-8-cyclopentyl-5-methyl-2-(5-piperazin-1-yl-pyridin-2-ylamino)-8H-pyrido[2,3-d]pyrimidin-7-one which can be characterized by XRPD patterns including diffraction peaks, measured using CuKα radiation, at at least one 2θ value of 13.3±0.2, 19.3±0.2, 25.7±0.2, 23.7±0.2, or 8.52±0.2. In some embodiments, the X-ray powder diffraction pattern further includes diffraction peaks, measured using CuKα radiation, at 2θ values of 18.9±0.2, 22.3±0.2, 11.5±0.2, 17.3±0.2, 21.6±0.2, 26.9±0.2, and 18.6±0.2. In some embodiments, the X-ray powder diffraction pattern further includes diffraction peaks, measured using CuKα radiation, at 2θ values of 24.3±0.2, 23.5±0.2, 9.9±0.2, 17.7±0.2, 43.9±0.2, 31.4±0.2, 37.1±0.2, and 27.9±0.2.

Some embodiments of the present disclosure provide the crystal Form VI of 6-Acetyl-8-cyclopentyl-5-methyl-2-(5-piperazin-1-yl-pyridin-2-ylamino)-8H-pyrido[2,3-d]pyrimidin-7-one which can be characterized by XRPD patterns including diffraction peaks, measured using CuKα radiation, at at least one 2θ value of 22.3±0.2, 19.5±0.2, 10.1±0.2, 16.9±0.2, or 10.7±0.2. In some embodiments, the X-ray powder diffraction pattern further includes diffraction peaks, measured using CuKα radiation, at 2θ values of 18.6±0.2, 21.7±0.2, 7.8±0.2, 11.4±0.2, and 15.8±0.2. In some embodiments, the X-ray powder diffraction pattern further includes diffraction peaks, measured using CuKα radiation, at 2θ values of 28.4±0.2, 9.1±0.2, 13.0±0.2, 17.4±0.2, 13.9±0.2, and 13.6±0.2.

Some embodiments of the present disclosure provide the crystal Form VII of 6-Acetyl-8-cyclopentyl-5-methyl-2-(5-piperazin-1-yl-pyridin-2-ylamino)-8H-pyrido[2,3-d]pyrimidin-7-one which can be characterized by XRPD patterns including diffraction peaks, measured using CuKα radiation, at at least one 2θ value of 17.6±0.2, 19.4±0.2, 7.8±0.2, 9.7±0.2, or 12.0±0.2. In some embodiments, the X-ray powder diffraction pattern further includes diffraction peaks, measured using CuKα radiation, at 2θ values of 12.8±0.2, 22.2±0.2, 17.1±0.2, 15.6±0.2, 25.4±0.2, and 24.0±0.2.

Some embodiments of the present disclosure provide the crystal Form VIII of 6-Acetyl-8-cyclopentyl-5-methyl-2-(5-piperazin-1-yl-pyridin-2-ylamino)-8H-pyrido[2,3-d]pyrimidin-7-one which can be characterized by XRPD patterns including diffraction peaks, measured using CuKα radiation, at at least one 2θ value of 10.3±0.2, 10.0±0.2, 21.6±0.2, 12.0±0.2, or 20.5±0.2. In some embodiments, the X-ray powder diffraction pattern further includes diffraction peaks, measured using CuKα radiation, at 2θ values of 20.9±0.2, 17.5±0.2, 14.0±0.2, 18.9±0.2, and 31.6±0.2. In some embodiments, the X-ray powder diffraction pattern further includes diffraction peaks, measured using CuKα radiation, at 2θ values of 7.8±0.2, 22.5±0.2, 18.6±0.2, 15.6±0.2, and 5.2±0.2.

Some embodiments of the present disclosure provide the crystal Form IX of 6-Acetyl-8-cyclopentyl-5-methyl-2-(5-piperazin-1-yl-pyridin-2-ylamino)-8H-pyrido[2,3-d]pyrimidin-7-one which can be characterized by XRPD patterns including diffraction peaks, measured using CuKα radiation, at at least one 2θ value of 22.2±0.2, 19.5±0.2, 17.3±0.2, 10.2±0.2, or 12.4±0.2. In some embodiments, the X-ray powder diffraction pattern further includes diffraction peaks, measured using CuKα radiation, at 2θ values of 19.2±0.2, 20.7±0.2, 8.2±0.2, 28.1±0.2, and 13.2±0.2. In some embodiments, the X-ray powder diffraction pattern further includes diffraction peaks, measured using CuKα radiation, at 2θ values of 33.5±0.2, 29.8±0.2, 18.0±0.2, 9.7±0.2, 15.9±0.2, 28.6±0.2, and 24.9±0.2.

Some embodiments of the present disclosure provide the crystal Form X of 6-Acetyl-8-cyclopentyl-5-methyl-2-(5-piperazin-1-yl-pyridin-2-ylamino)-8H-pyrido[2,3-d]pyrimidin-7-one which can be characterized by XRPD patterns including diffraction peaks, measured using CuKα radiation, at at least one 2θ value of 7.7±0.2, 13.5±0.2, 21.8±0.2, 16.3±0.2, or 8.6±0.2. In some embodiments, the X-ray powder diffraction pattern further includes diffraction peaks, measured using CuKα radiation, at 2θ values of 17.4±0.2, 11.7±0.2, 19.2±0.2, 18.8±0.2, and 10.0±0.2. In some embodiments, the X-ray powder diffraction pattern further includes diffraction peaks, measured using CuKα radiation, at 2θ values of 20.2±0.2, 23.8±0.2, 24.3±0.2, 22.5±0.2, 27.3±0.2, 23.4±0.2, 26.1±0.2, 19.7±0.2, and 15.0±0.2.

Some embodiments of the present disclosure provide the crystal Form XI of 6-Acetyl-8-cyclopentyl-5-methyl-2-(5-piperazin-1-yl-pyridin-2-ylamino)-8H-pyrido[2,3-d]pyrimidin-7-one which can be characterized by XRPD patterns including diffraction peaks, measured using CuKα radiation, at at least one 2θ value of 21.5±0.2, 23.0±0.2, 19.5±0.2, 10.8±0.2, or 20.0±0.2. In some embodiments, the X-ray powder diffraction pattern further includes diffraction peaks, measured using CuKα radiation, at 2θ values of 16.9±0.2, 13.1±0.2, 25.4±0.2, 9.1±0.2, 15.8±0.2, and 18.4±0.2. In some embodiments, the X-ray powder diffraction pattern further includes diffraction peaks, measured using CuKα radiation, at 2θ values of 15.3±0.2, 9.6±0.2, 24.0±0.2, 26.4±0.2, 26.7±0.2, and 27.9±0.2.

Some embodiments of the present disclosure provide the crystal Form XII of 6-Acetyl-8-cyclopentyl-5-methyl-2-(5-piperazin-1-yl-pyridin-2-ylamino)-8H-pyrido[2,3-d]pyrimidin-7-one which can be characterized by XRPD patterns including diffraction peaks, measured using CuKα radiation, at at least one 2θ value of 10.0±0.2, 10.9±0.2, 9.0±0.2, 19.3±0.2, or 13.5±0.2. In some embodiments, the X-ray powder diffraction pattern further includes diffraction peaks, measured using CuKα radiation, at 2θ values of 22.3±0.2, 22.7±0.2, 17.0±0.2, 11.4±0.2, and 19.5±0.2. In some embodiments, the X-ray powder diffraction pattern further includes diffraction peaks, measured using CuKα radiation, at 2θ values of 12.8±0.2, 18.1±0.2, 20.1±0.2, 9.6±0.2, 25.9±0.2, 15.5±0.2, 18.5±0.2, 29.8±0.2, 20.5±0.2, 7.8±0.2, and 13.9±0.2.

Some embodiments of the present disclosure provide the crystal Form XIV of 6-Acetyl-8-cyclopentyl-5-methyl-2-(5-piperazin-1-yl-pyridin-2-ylamino)-8H-pyrido[2,3-d]pyrimidin-7-one which can be characterized by XRPD patterns including diffraction peaks, measured using CuKα radiation, at at least one 2θ value of 21.4±0.2, 22.4±0.2, 10.1±0.2, 22.2±0.2, or 10.0±0.2. In some embodiments, the X-ray powder diffraction pattern further includes diffraction peaks, measured using CuKα radiation, at 2θ values of 17.8±0.2, 18.6±0.2, 20.4±0.2, 19.6±0.2, 11.4±0.2, and 17.1±0.2. In some embodiments, the X-ray powder diffraction pattern further includes diffraction peaks, measured using CuKα radiation, at 2θ values of 17.4±0.2, 7.9±0.2, 21.0±0.2, 11.8±0.2, 25.1±0.2, 15.9±0.2, 20.1±0.2, 22.9±0.2, 11.0±0.2, 13.9±0.2, 13.5±0.2, and 23.7±0.2.

Another aspect of the present disclosure provides a method using any of the 6-acetyl-8-cyclopentyl-5-methyl-2-(5-piperazin-1-yl-pyridin-2-ylamino)-8H-pyrido[2,3-d]pyrimidine-7-one crystals of crystal Forms I, II, III, IV, V, VI, VII, VIII, IX, X, XI, XII and XIV as active ingredients, and uses thereof for pharmaceutical composition for treatment of patients with Estrogen receptor (ER)-positive, human epidermal growth factor receptor-2 (HER2)-negative, or advanced breast cancer in postmenopausal women.

The beneficial effects of the present disclosure compared to the prior art may include: the solubility and dissolution rate of palbociclib crystal Form VIII, XI, XIV in pH 6.8 buffer are greater than the existing crystal Forms A and B. Therefore, in terms of solubility, the new crystal Form may have obvious advantages over the existing crystal Form.

[2,3-d]pyrimidin-7-one Form X. Temperature in unit of 0 C in accordance with the abscissa. The Heat flow (w/g) as ordinate.

Figure 23:
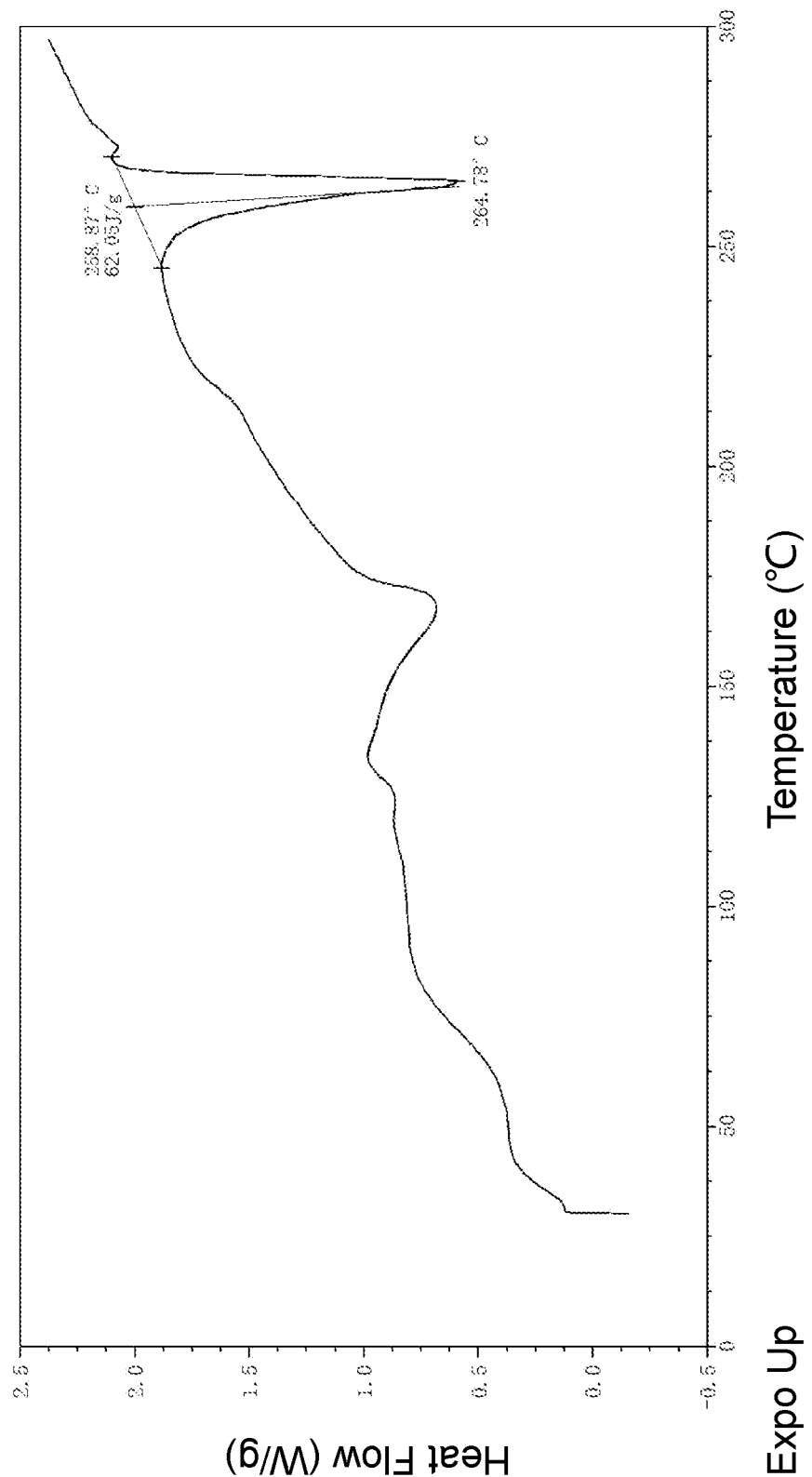

FIG. 23 is a DSC plot of 6-Acetyl-8-cyclopentyl-5-methyl-2-(5-piperazin-1-yl-pyridin-2-ylamino)-8H-pyrido [2,3-d]pyrimidin-7-one Form XI. Temperature in unit of 0 C in accordance with the abscissa. The Heat flow (w/g) as ordinate.

Figure 24:
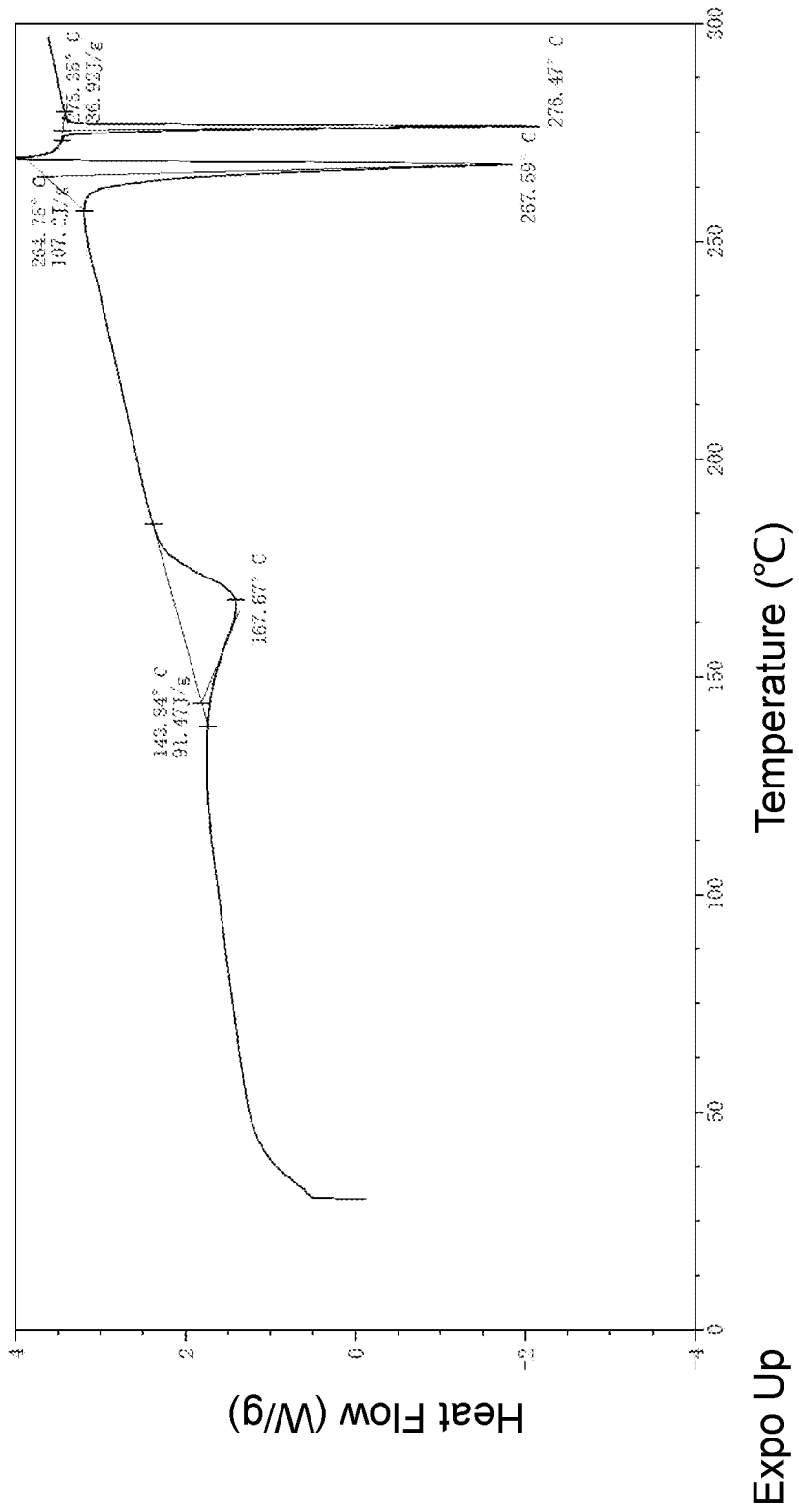

FIG. 24 is a DSC plot of 6-Acetyl-8-cyclopentyl-5-methyl-2-(5-piperazin-1-yl-pyridin-2-ylamino)-8H-pyrido [2,3-d]pyrimidin-7-one Form XII. Temperature in unit of 0 C in accordance with the abscissa. The Heat flow (w/g) as ordinate.

Figure 25:
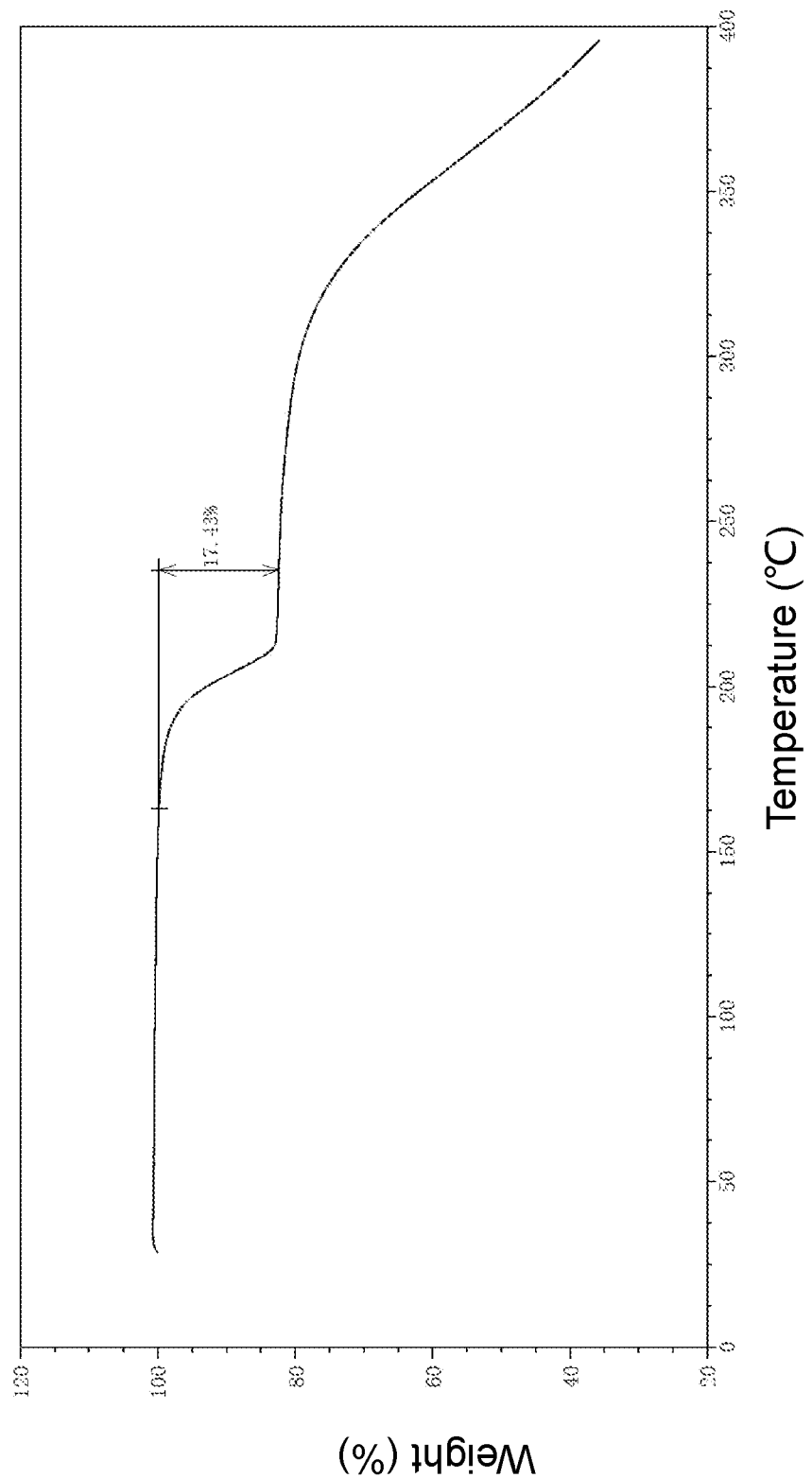

FIG. 25 is a TGA plot of 6-Acetyl-8-cyclopentyl-5-methyl-2-(5-piperazin-1-yl-pyridin-2-ylamino)-8H-pyrido [2,3-d]pyrimidin-7-one Form I. Temperature in unit of 0 C in accordance with the abscissa. The Weight (%) as ordinate.

Figure 26:
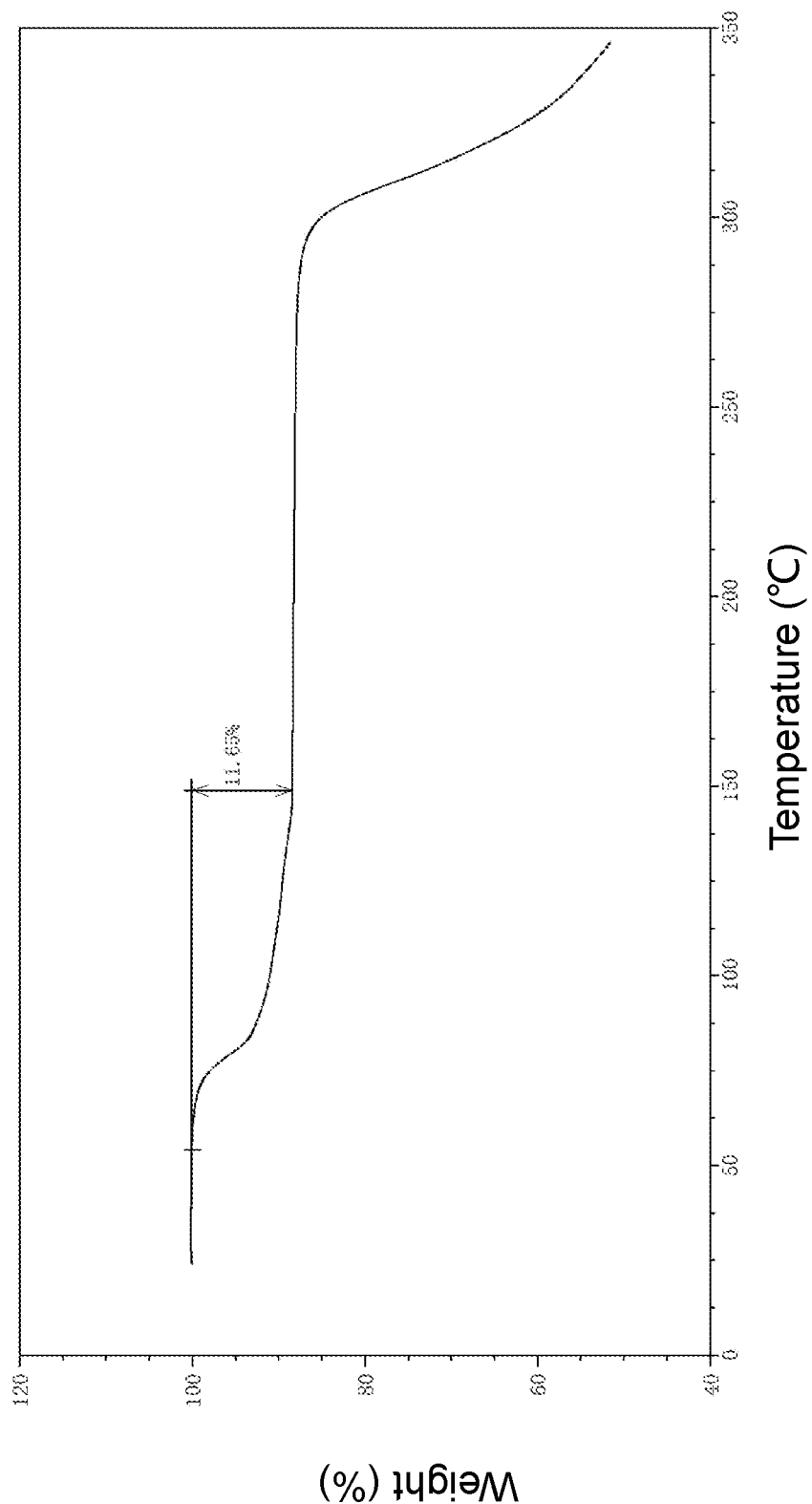

FIG. 26 is a TGA plot of 6-Acetyl-8-cyclopentyl-5-methyl-2-(5-piperazin-1-yl-pyridin-2-ylamino)-8H-pyrido [2,3-d]pyrimidin-7-one Form II. Temperature in unit of 0 C in accordance with the abscissa. The Weight (%) as ordinate.

Figure 27:
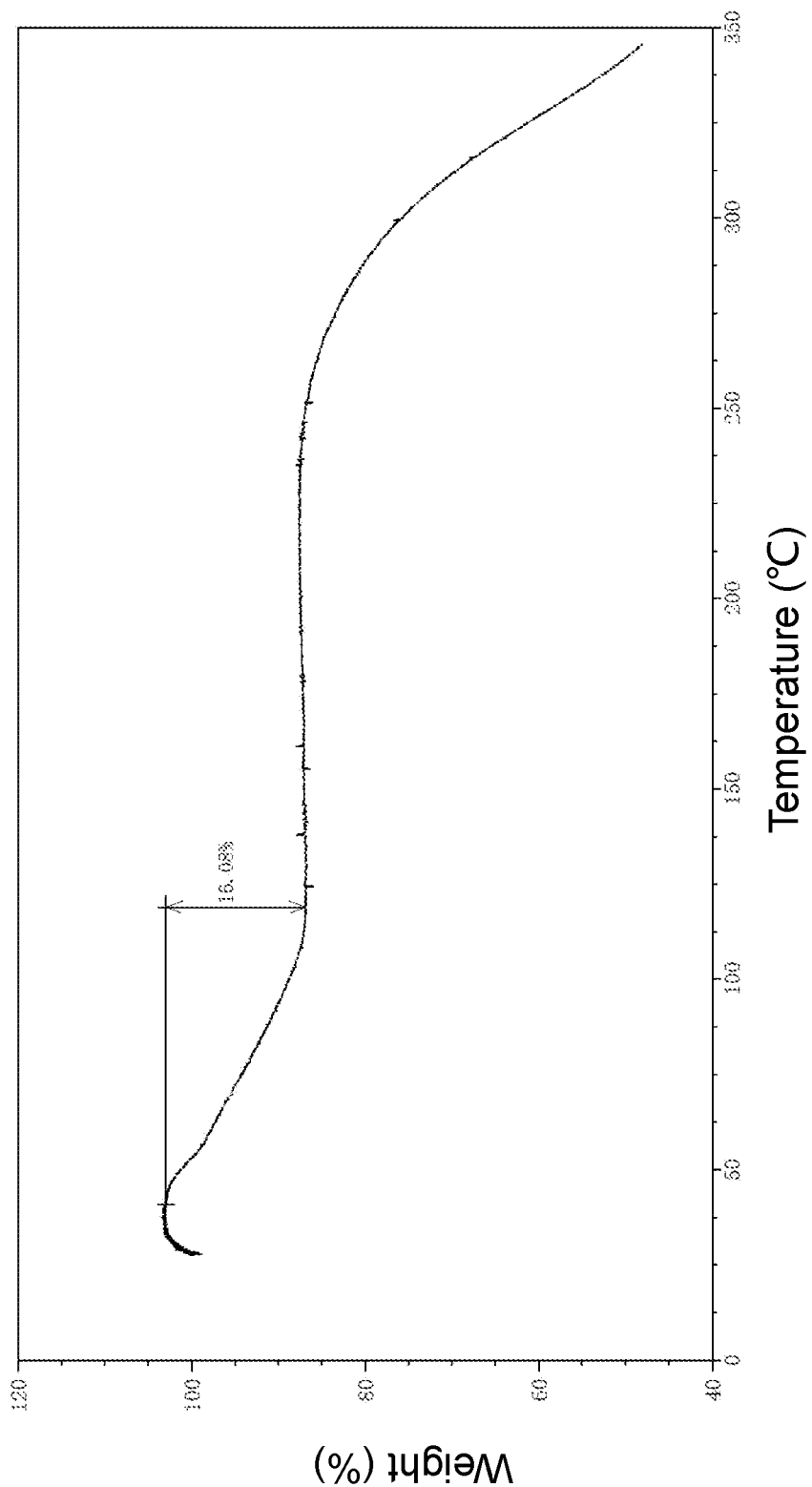

FIG. 27 is a TGA plot of 6-Acetyl-8-cyclopentyl-5-methyl-2-(5-piperazin-1-yl-pyridin-2-ylamino)-8H-pyrido [2,3-d]pyrimidin-7-one Form III. Temperature in unit of 0 C in accordance with the abscissa. The Weight (%) as ordinate.

Figure 28:
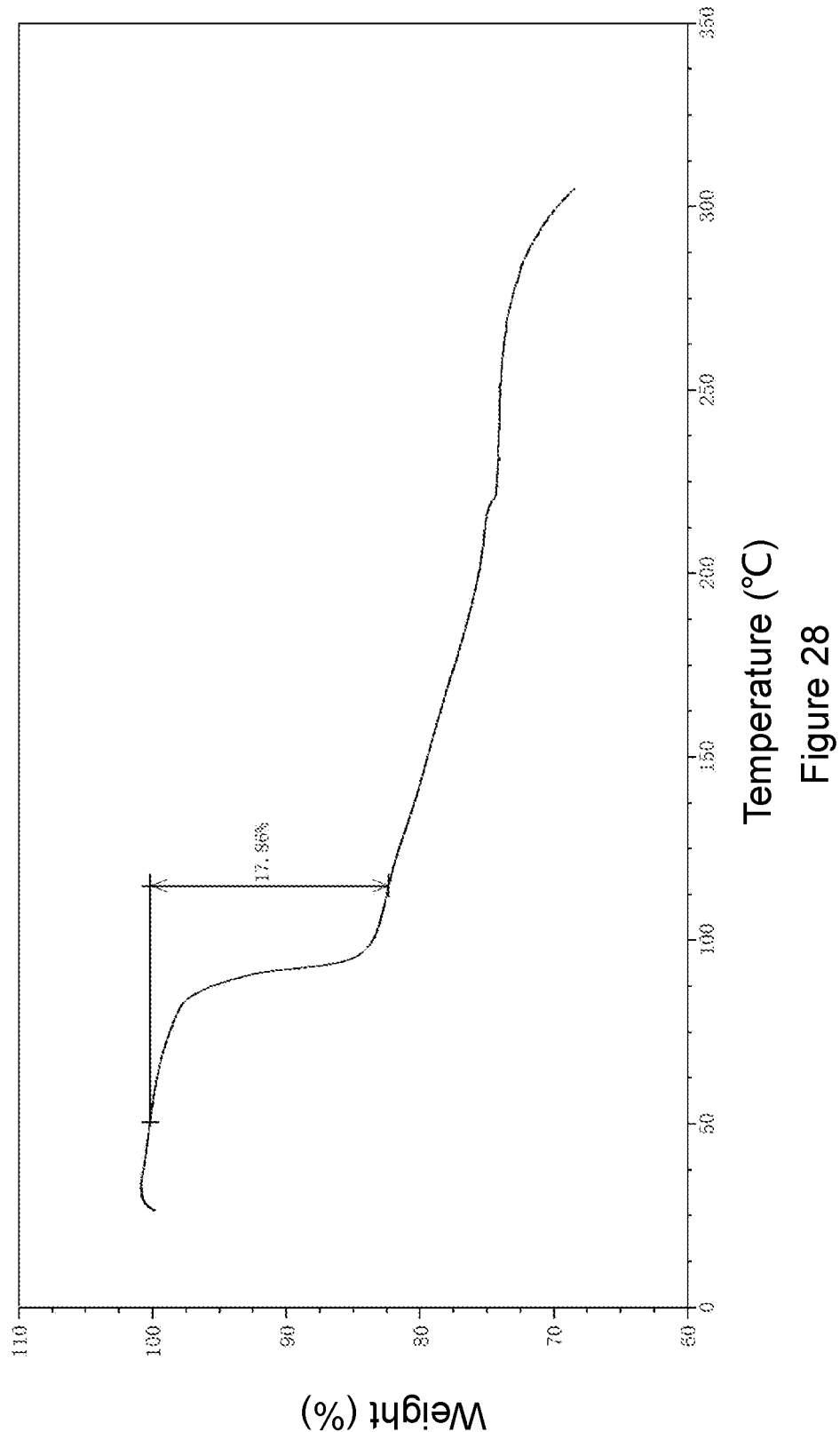

FIG. 28 is a TGA plot of 6-Acetyl-8-cyclopentyl-5-methyl-2-(5-piperazin-1-yl-pyridin-2-ylamino)-8H-pyrido [2,3-d]pyrimidin-7-one Form IV. Temperature in unit of 0 C in accordance with the abscissa. The Weight (%) as ordinate.

Figure 29:
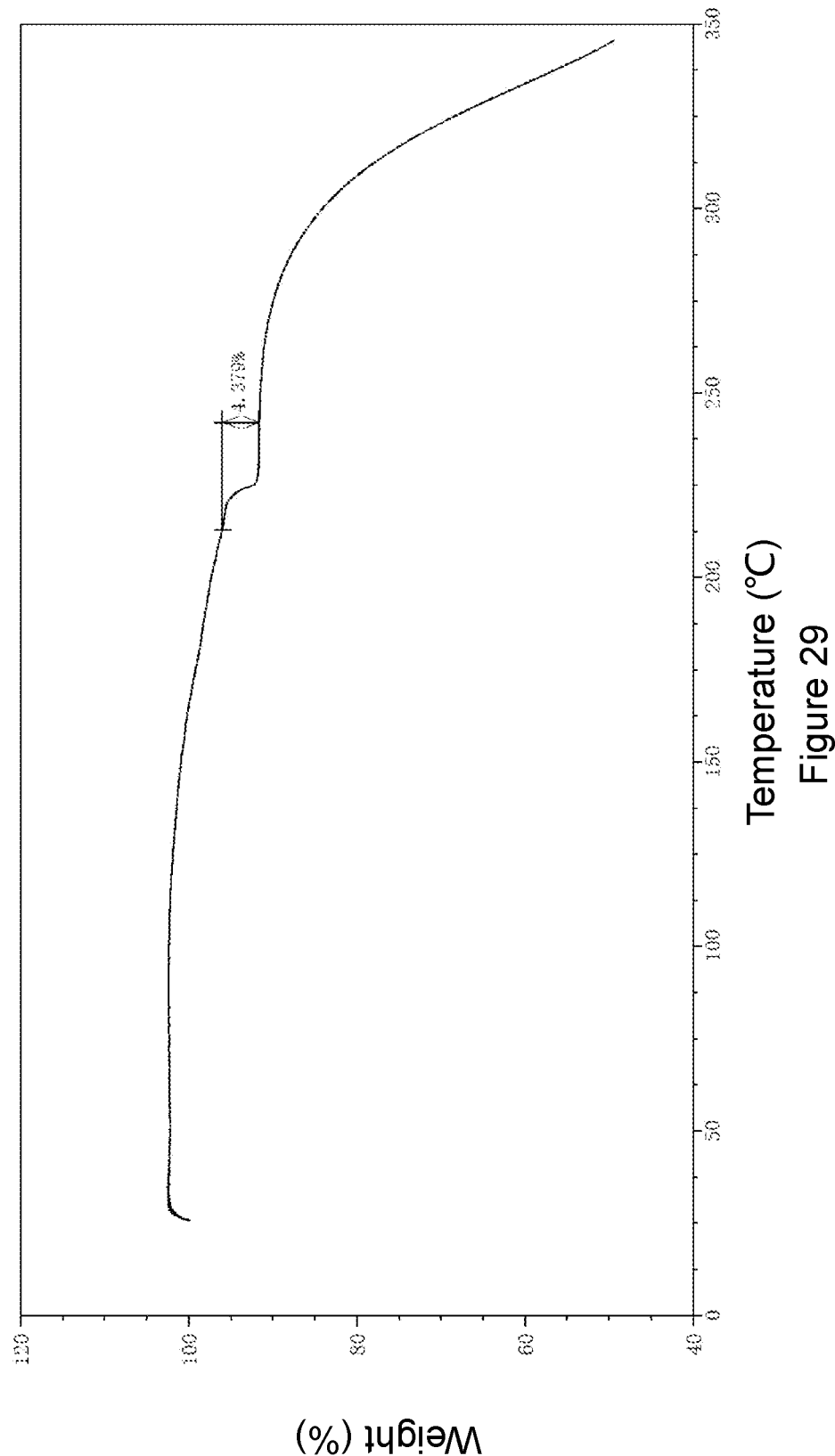

FIG. 29 is a TGA plot of 6-Acetyl-8-cyclopentyl-5-methyl-2-(5-piperazin-1-yl-pyridin-2-ylamino)-8H-pyrido [2,3-d]pyrimidin-7-one Form V. Temperature in unit of 0 C in accordance with the abscissa. The Weight (%) as ordinate.

Figure 30:
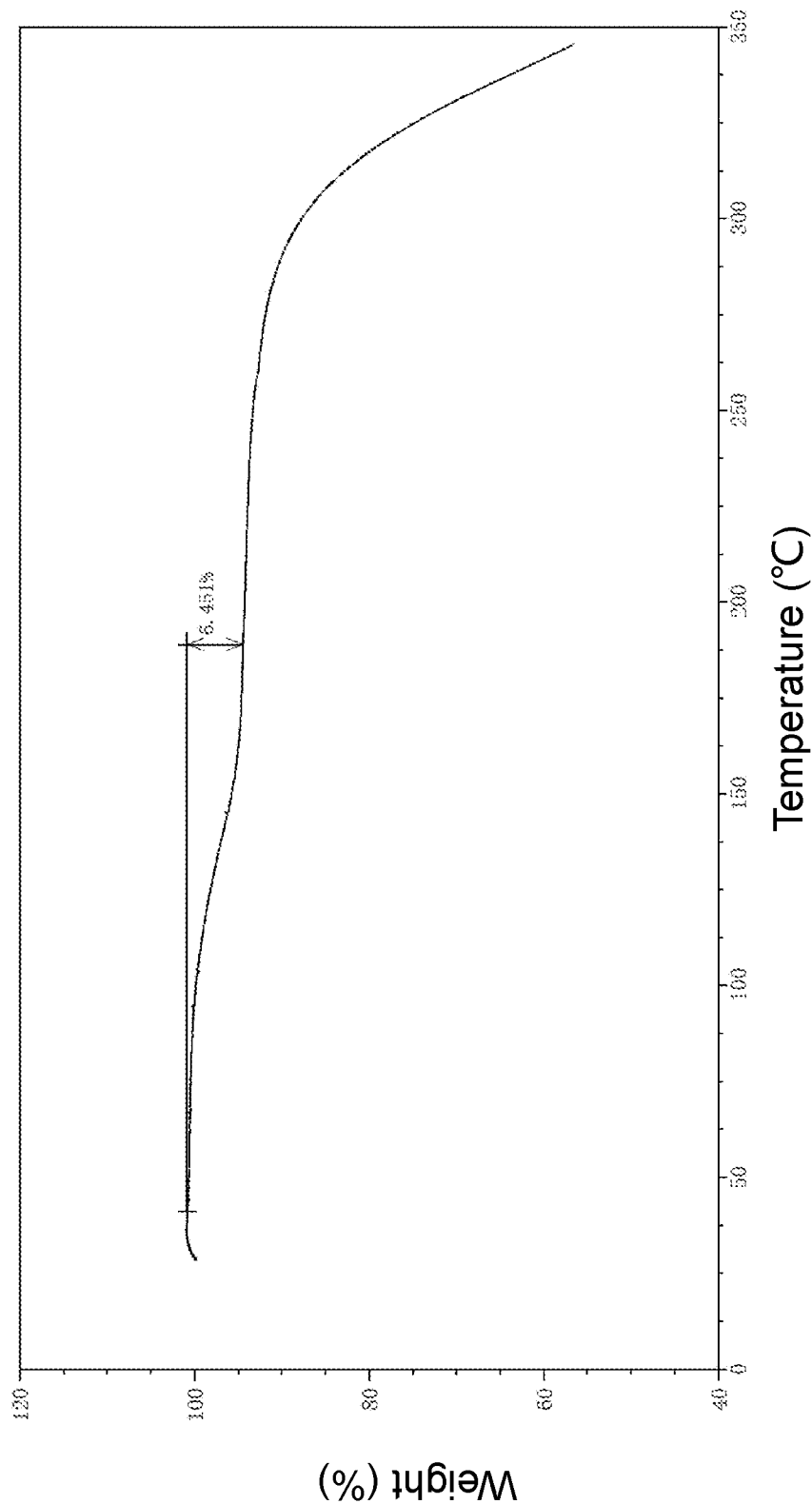

FIG. 30 is a TGA plot of 6-Acetyl-8-cyclopentyl-5-methyl-2-(5-piperazin-1-yl-pyridin-2-ylamino)-8H-pyrido [2,3-d]pyrimidin-7-one Form VI. Temperature in unit of 0 C in accordance with the abscissa. The Weight (%) as ordinate.

Figure 31:
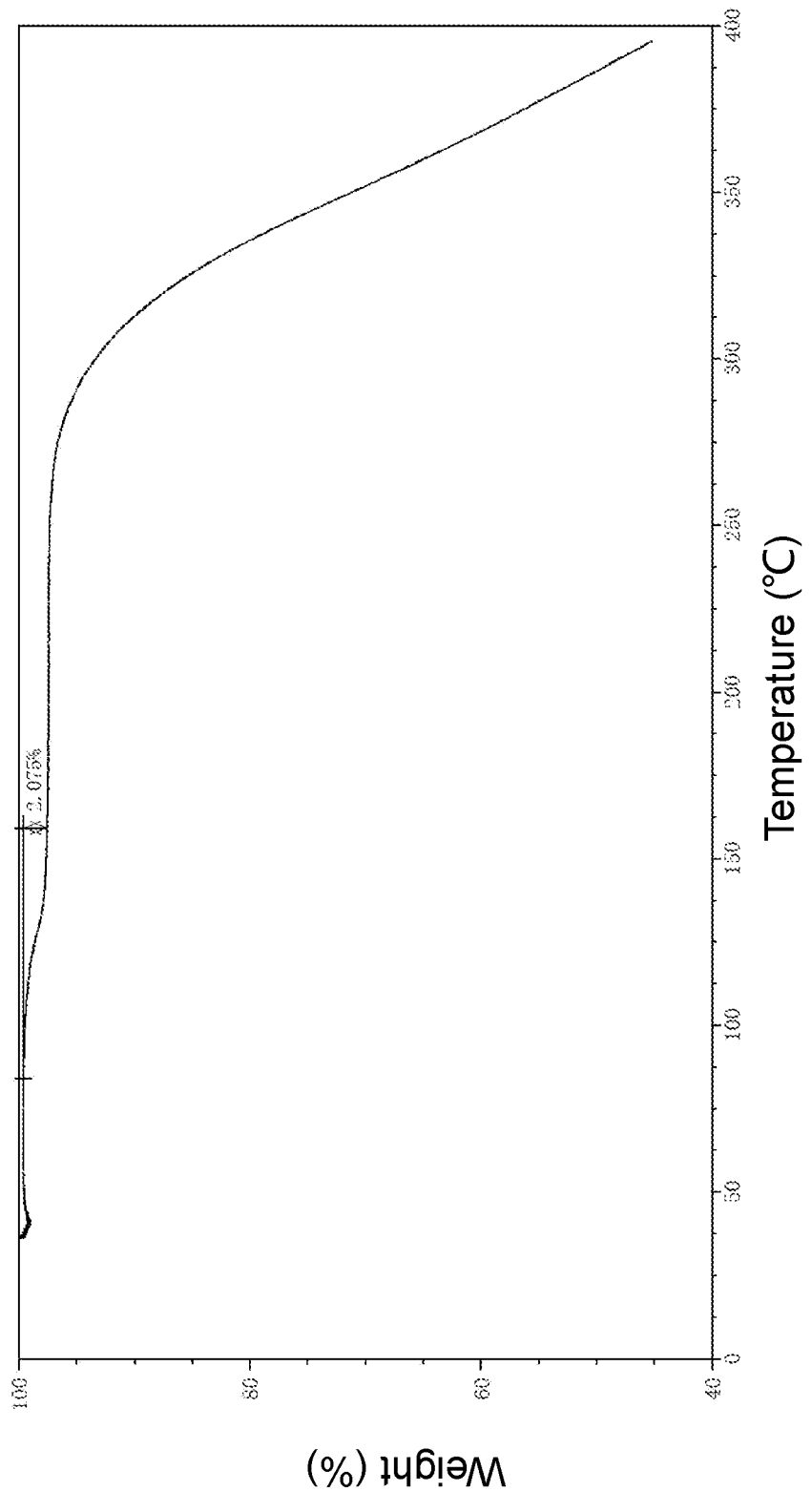

FIG. 31 is a TGA plot of 6-Acetyl-8-cyclopentyl-5-methyl-2-(5-piperazin-1-yl-pyridin-2-ylamino)-8H-pyrido [2,3-d]pyrimidin-7-one Form VIII. Temperature in unit of 0 C in accordance with the abscissa. The Weight (%) as ordinate.

Figure 32:
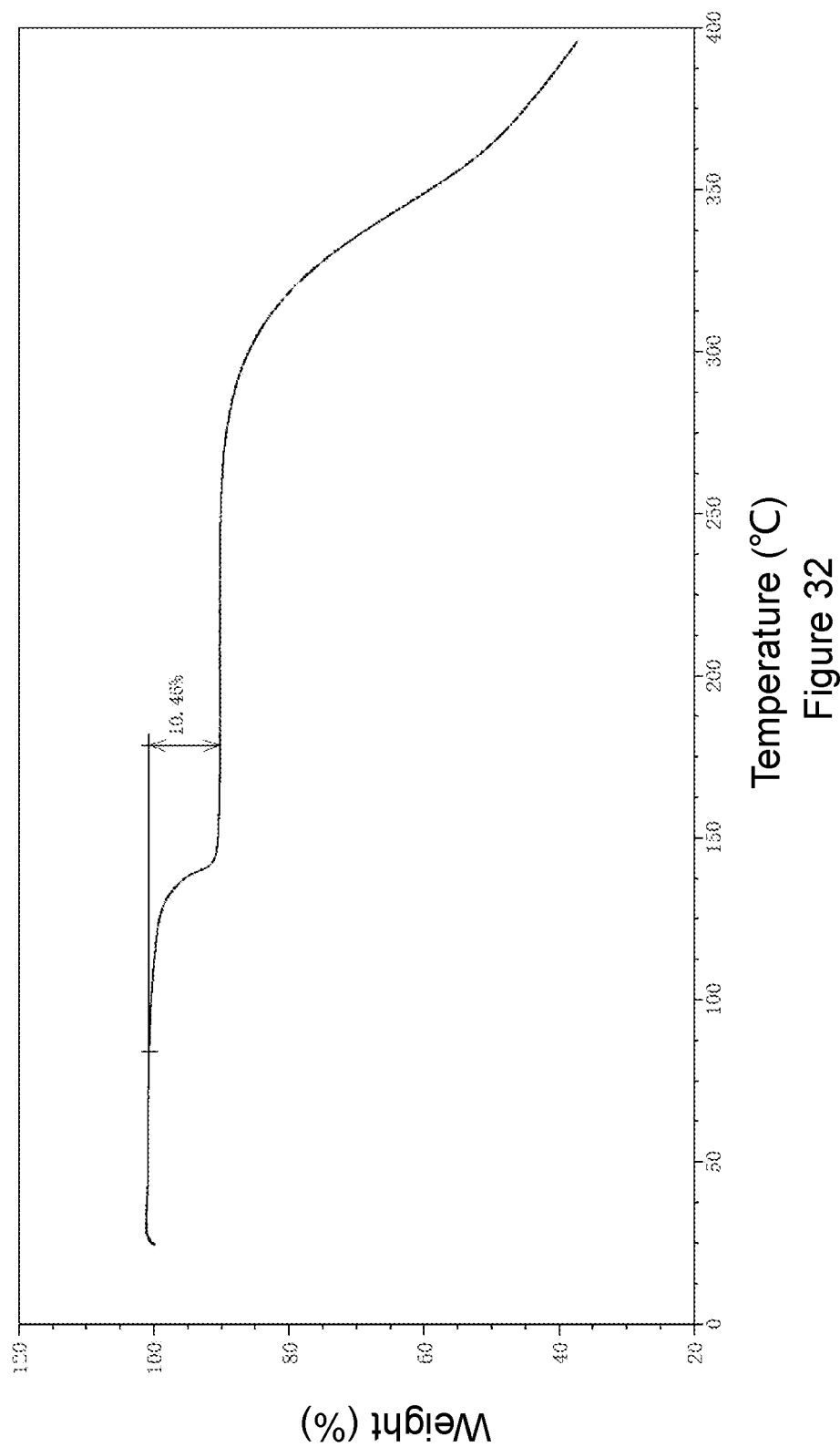

FIG. 32 is a TGA plot of 6-Acetyl-8-cyclopentyl-5-methyl-2-(5-piperazin-1-yl-pyridin-2-ylamino)-8H-pyrido [2,3-d]pyrimidin-7-one Form IX. Temperature in unit of 0 C in accordance with the abscissa. The Weight (%) as ordinate.

Figure 33:
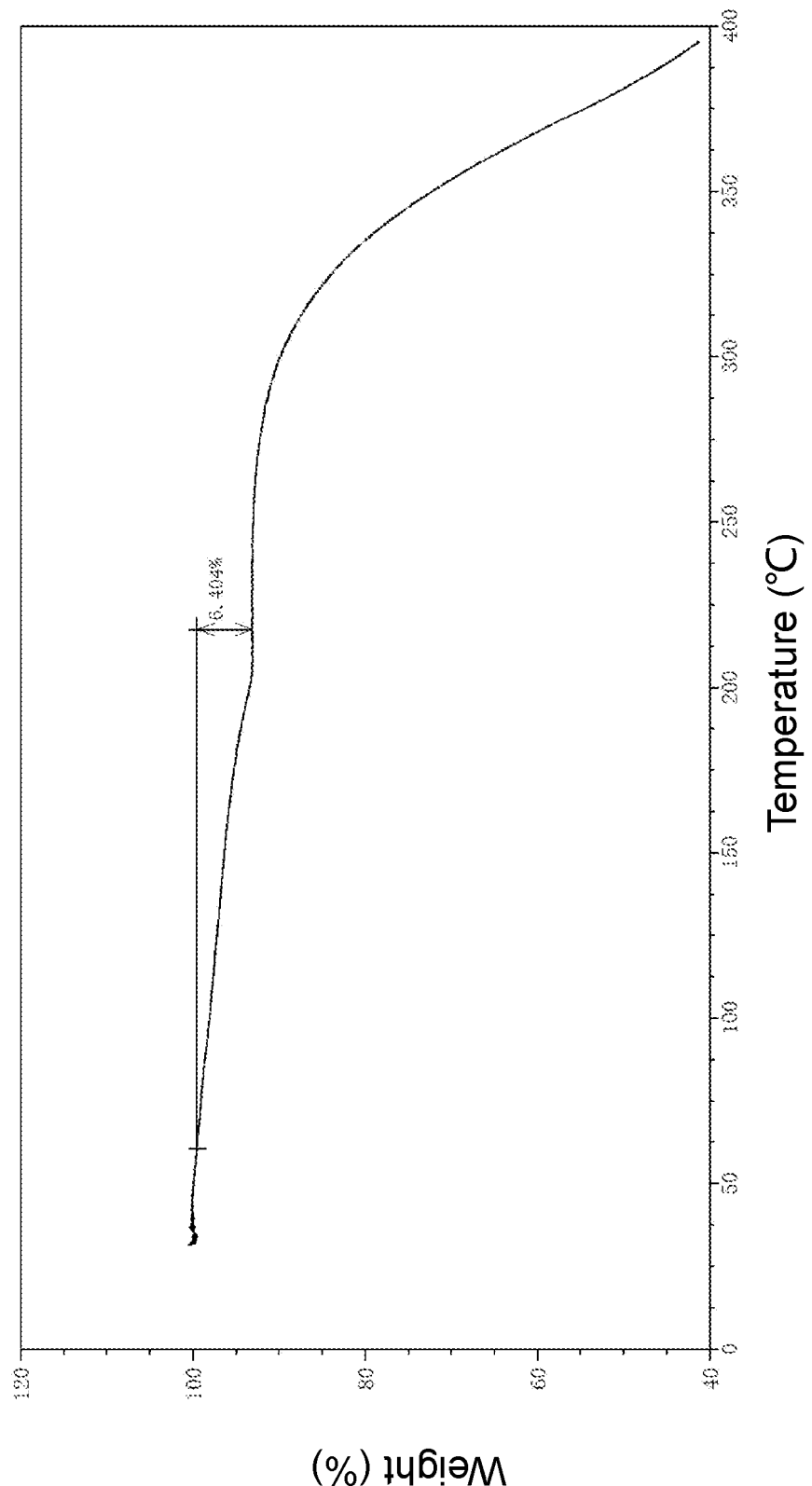

FIG. 33 is a TGA plot of 6-Acetyl-8-cyclopentyl-5-methyl-2-(5-piperazin-1-yl-pyridin-2-ylamino)-8H-pyrido [2,3-d]pyrimidin-7-one Form X. Temperature in unit of 0 C in accordance with the abscissa. The Weight (%) as ordinate.

Figure 34:
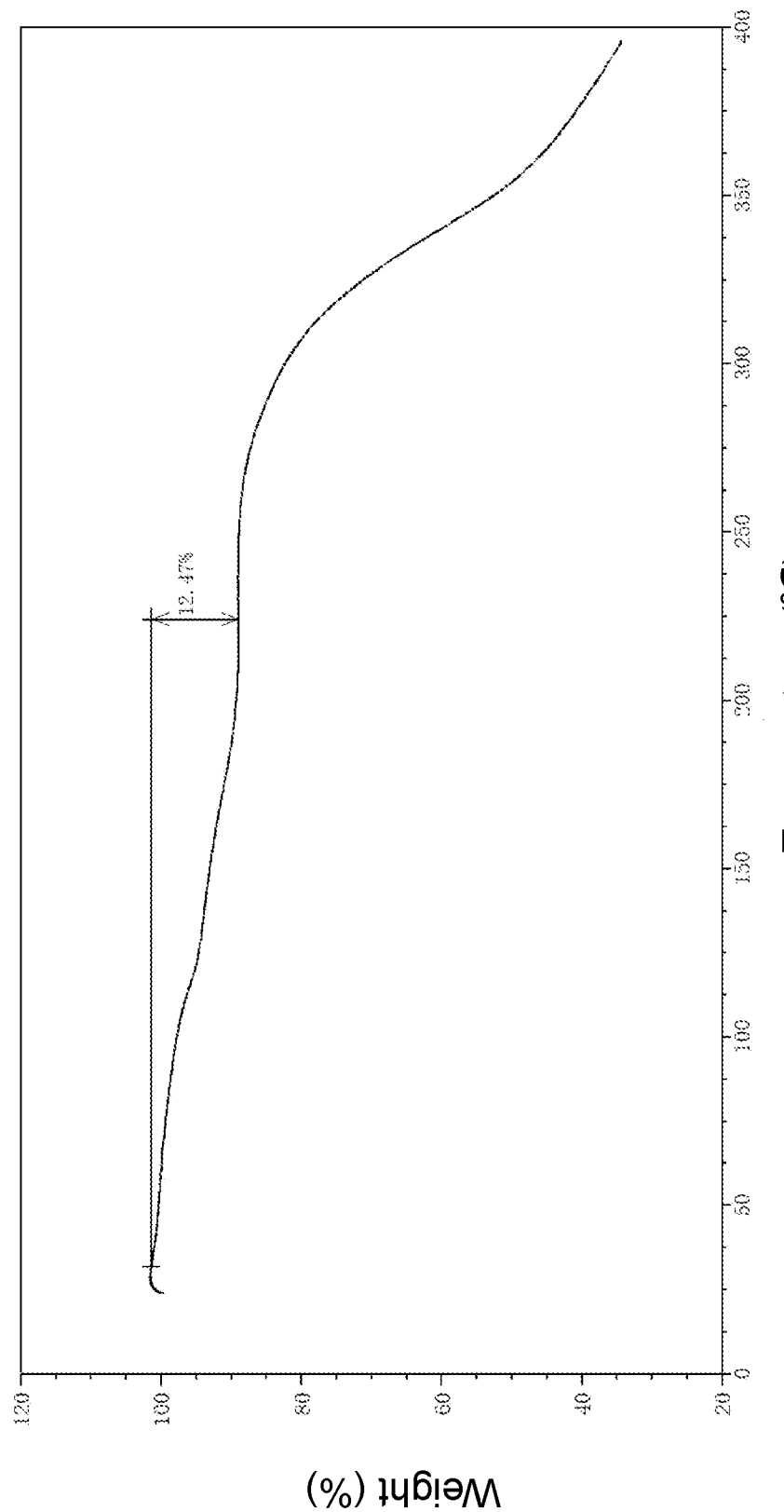

FIG. 34 is a TGA plot of 6-Acetyl-8-cyclopentyl-5-methyl-2-(5-piperazin-1-yl-pyridin-2-ylamino)-8H-pyrido [2,3-d]pyrimidin-7-one Form XI. Temperature in unit of 0 C in accordance with the abscissa. The Weight (%) as ordinate.

Figure 35:
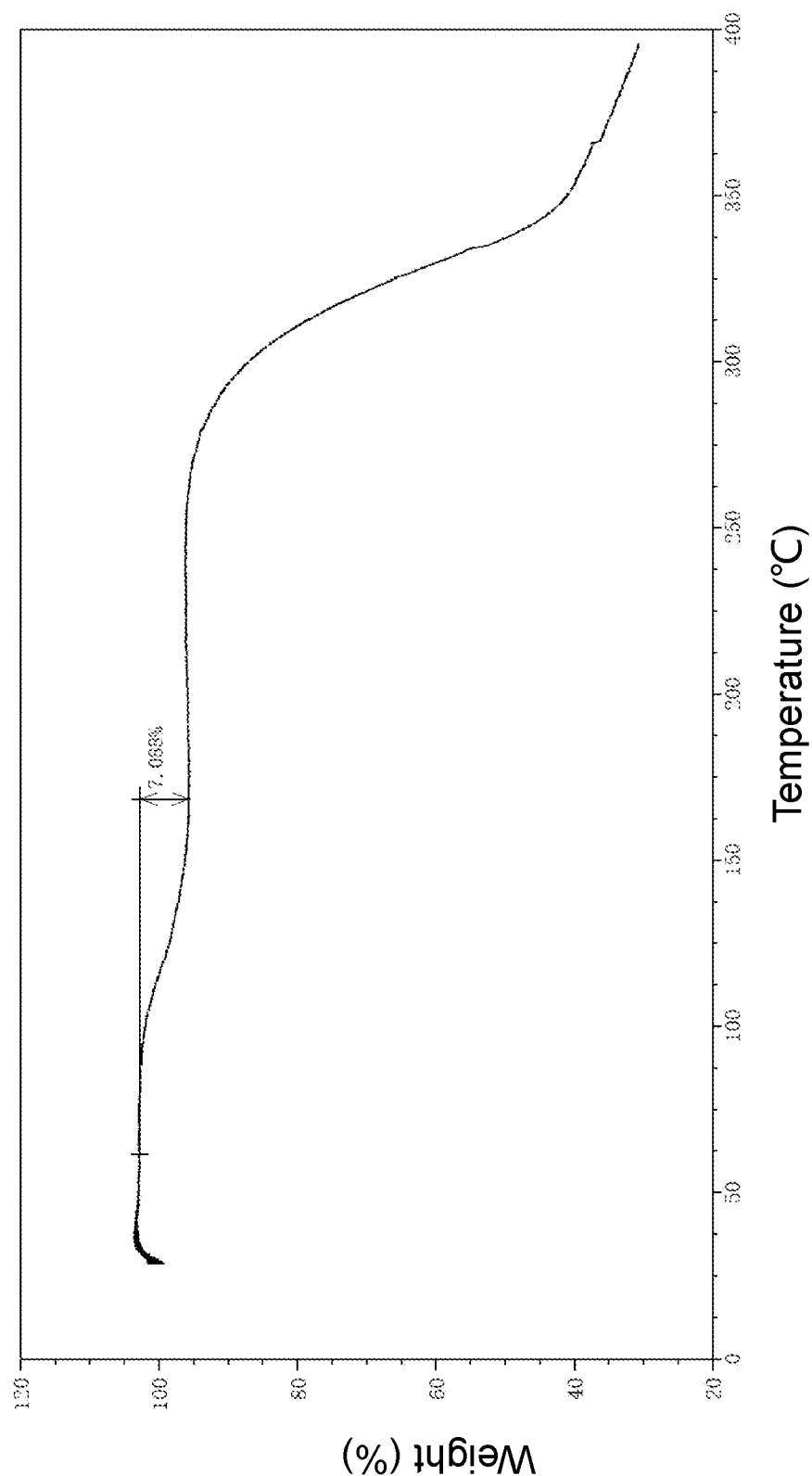

FIG. 35 is a TGA plot of 6-Acetyl-8-cyclopentyl-5-methyl-2-(5-piperazin-1-yl-pyridin-2-ylamino)-8H-pyrido [2,3-d]pyrimidin-7-one Form XII. Temperature in unit of 0 C in accordance with the abscissa. The Weight (%) as ordinate.

DETAILED DESCRIPTION

The specific embodiments of the present disclosure are further described in detail below with reference to the drawings and embodiments. The following examples are intended to illustrate the present disclosure, but are not intended to limit the scope of the present disclosure. The X-ray powder diffraction operations and analysis operations in the present disclosure include as follows:

The Rigaku Ultima IV powder diffractometer was used, which was irradiated with Cu—K(R) (40 kV, 40 mA) at room temperature using a D/tex Ultra detector. The scanning range is from 3° to 45° in the 2θ interval, and the scanning speed is 20°/min.

Measurement differences associated with X-ray powder diffraction analysis results are produced by a variety of factors including: (a) errors in sample preparation (eg, sample height), (b) instrument error, (c) calibration differences, (d) operator error (including errors that occur when determining peak position), and (e) properties of the substance (eg, preferred orientation error). Calibration errors and sample height errors often result in displacement of all peaks in the same direction. When using a flat sampler, small differences in sample height may result in large displacements of the XRPD peak position. Systematic studies have shown that a 1 mm sample height difference can result in a 2θ peak shift of up to 10. These displacements can be identified from the X-ray diffraction pattern and can be eliminated by compensating for the displacement (using a system calibration factor for all peak position values) or recalibrating the instrument. As described above, the measurement errors from different instruments can be corrected by applying a system calibration factor to make the peak positions consistent.

A differential scanning calorimetry (DSC) analysis was performed on the crystal Forms in Examples, using a TA Q2000 differential scanning calorimeter using an $N_2$ atmosphere at a temperature rising rate of 10° C./min.

The thermogravimetric (TGA) analysis of the crystal Forms in Examples was carried out using a TA Q500 thermogravimetric analyzer using a $N_2$ atmosphere at a heating rate of 10° C./min.

Example 1

Figure 1:
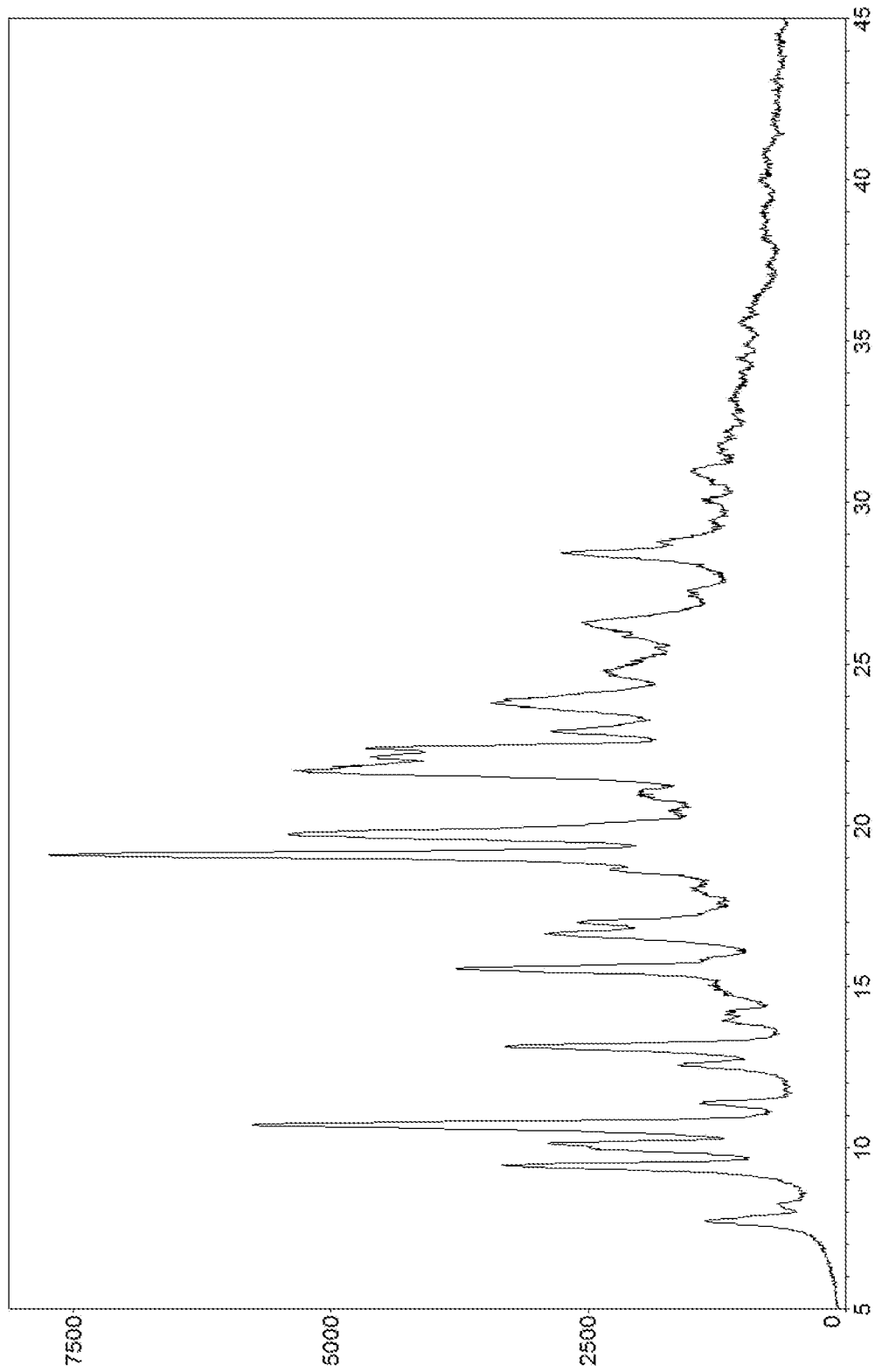
FIG. 1 is an XRPD pattern of 6-Acetyl-8-cyclopentyl-5-methyl-2-(5-piperazin-1-yl-pyridin-2-ylamino)-8H-pyrido[2,3-d]pyrimidin-7-one Form I. 2θ values in unit of degree in accordance with the abscissa. The intensity of diffraction peak as ordinate.

The crystal Form I of 6-Acetyl-8-cyclopentyl-5-methyl-2-(5-piperazin-1-yl-pyridin-2-ylamino)-8H-pyrido[2,3-d] pyrimidin-7-one was obtained after slurring of 1.0 g of 6-Acetyl-8-cyclopentyl-5-methyl-2-(5-piperazin-1-yl-pyridin-2-ylamino)-8H-pyrido[2,3-d]pyrimidin-7-one in 50 ml of diethyl oxalate for 24 hours. The XRPD pattern of the resulting crystal Form I is shown in FIG. 1 and information of diffraction peaks at 2θ values are listed in the following table:

| 2θ (degree) | d (Å) | I (Height) % |
| --- | --- | --- |
| 7.76 | 11.3838 | 20.2 |
| 8.297 | 10.6476 | 4.6 |
| 9.479 | 9.3224 | 50.6 |
| 10.141 | 8.7152 | 35.9 |
| 10.721 | 8.2454 | 86.2 |
| 11.401 | 7.7547 | 12.7 |
| 12.581 | 7.0299 | 17.4 |
| 13.141 | 6.7317 | 45.9 |
| 13.961 | 6.3383 | 8 |
| 15.579 | 5.6832 | 48.8 |
| 16.641 | 5.323 | 32.2 |
| 17.001 | 5.211 | 25.9 |
| 18.622 | 4.761 | 9.6 |
| 19.1 | 4.6429 | 100 |
| 19.74 | 4.4937 | 59.6 |
| 20.941 | 4.2387 | 6.3 |
| 21.699 | 4.0922 | 62.7 |
| 22.14 | 4.0118 | 48 |
| 22.381 | 3.969 | 46.8 |

-continued

| 2θ (degree) | d (Å) | I (Height) % |
|---|---|---|
| 22.921 | 3.8768 | 16 |
| 23.8 | 3.7355 | 26.1 |
| 24.8 | 3.5871 | 8.9 |
| 25.862 | 3.4422 | 8.2 |
| 26.299 | 3.3859 | 17.3 |
| 27.265 | 3.2681 | 4.2 |
| 28.459 | 3.1337 | 26.7 |
| 28.799 | 3.0975 | 10.8 |
| 30.117 | 2.9648 | 4.3 |
| 30.96 | 2.886 | 6.3 |

Figure 14:
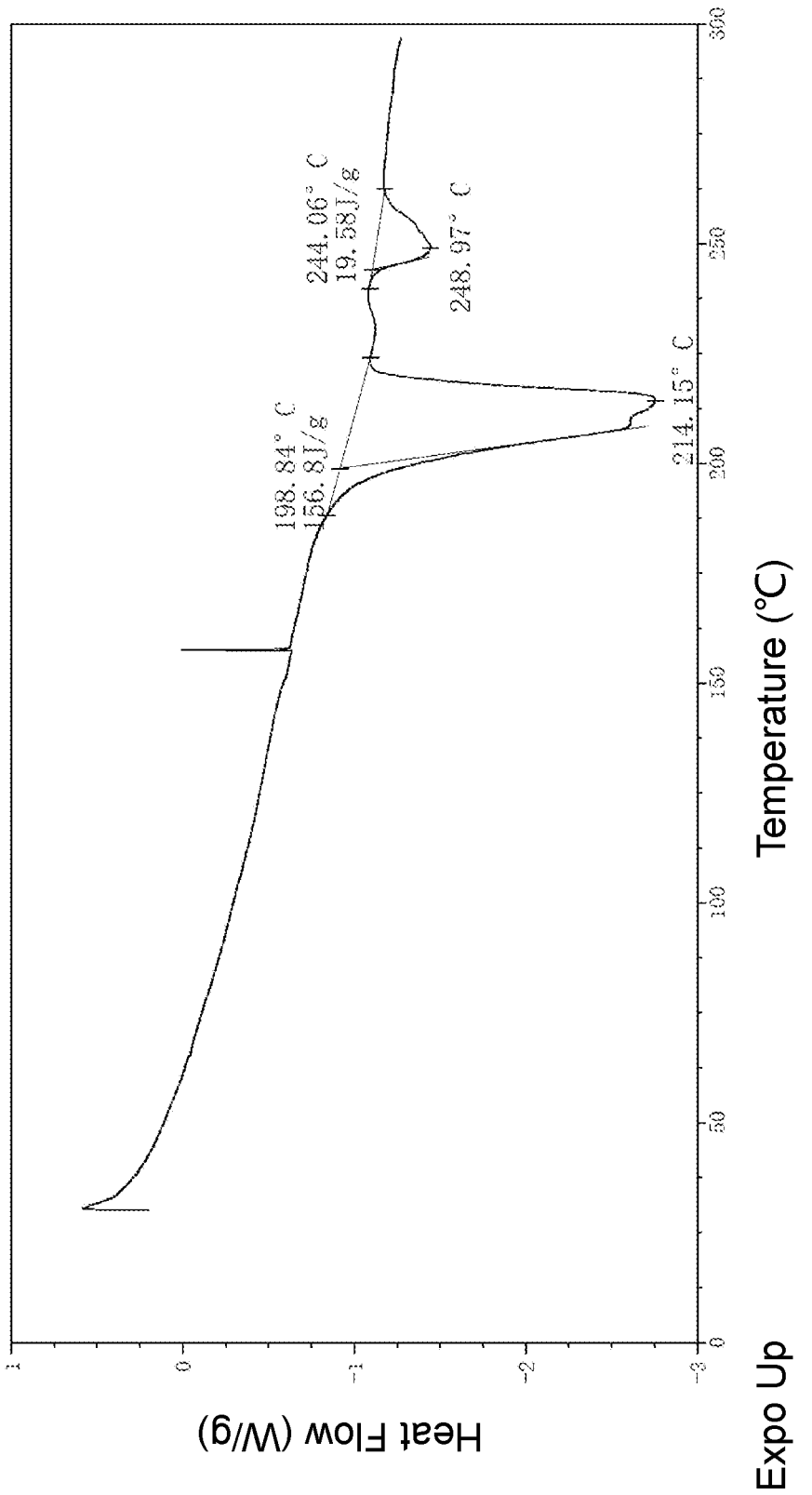
FIG. 14 is a DSC plot of 6-Acetyl-8-cyclopentyl-5-methyl-2-(5-piperazin-1-yl-pyridin-2-ylamino)-8H-pyrido[2,3-d]pyrimidin-7-one Form I. Temperature in unit of 0 C in accordance with the abscissa. The Heat flow (w/g) as ordinate.

A differential scanning calorimetry (DSC) analysis was performed on the crystal Form I in Example 1, using a TA Q2000 differential scanning calorimeter using an $N_2$ atmosphere at a temperature rising rate of 10° C./min. The DSC plot of Form I is shown in FIG. 14.

The thermogravimetric (TGA) analysis of the crystal Form I in Example 1 was carried out using a TA Q500 thermogravimetric analyzer using a $N_2$ atmosphere at a heating rate of 10° C./min. The TGA plot of Form I is shown in FIG. 25.

Example 2

Figure 2:
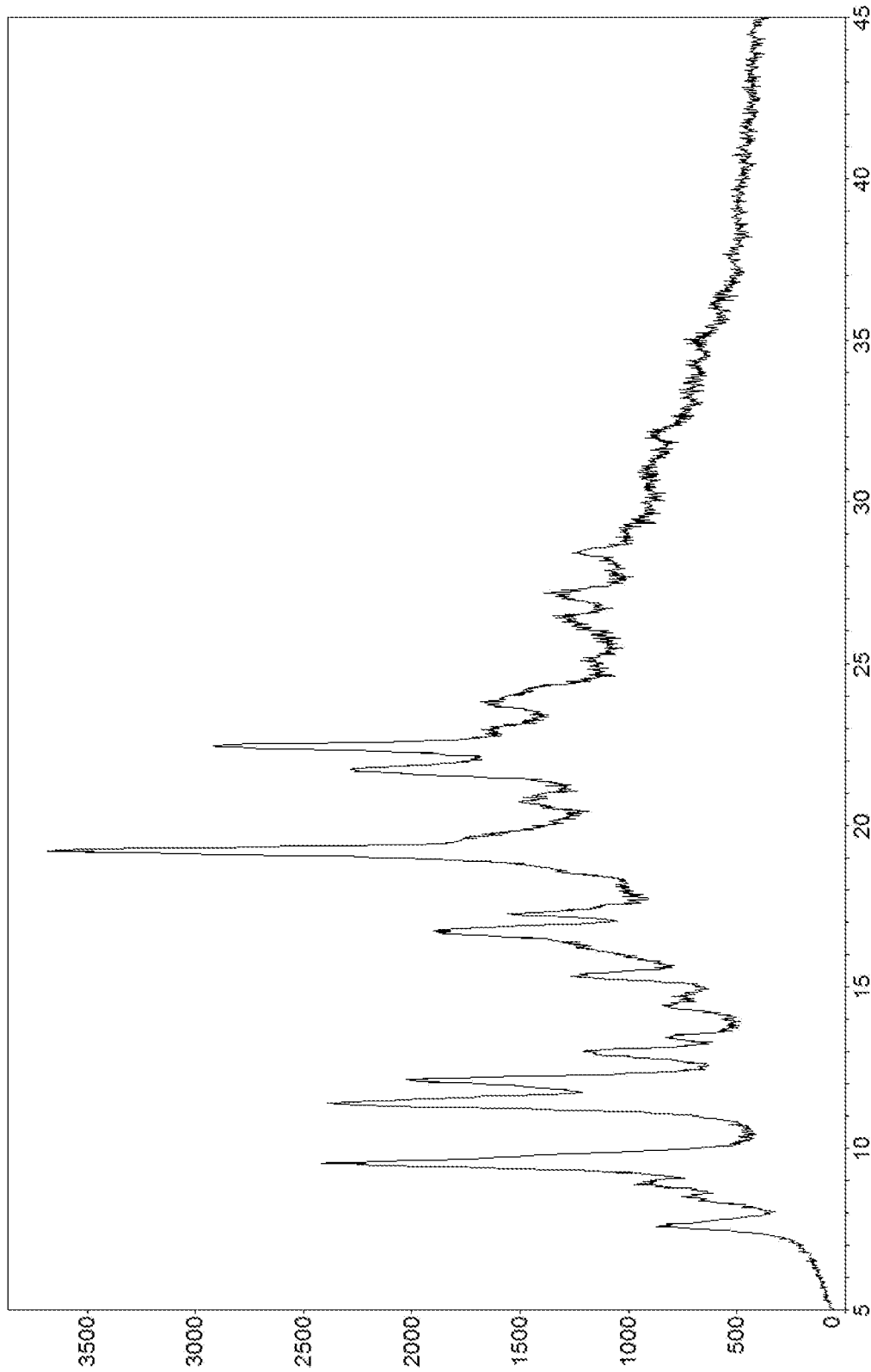
FIG. 2 is an XRPD pattern of 6-Acetyl-8-cyclopentyl-5-methyl-2-(5-piperazin-1-yl-pyridin-2-ylamino)-8H-pyrido[2,3-d]pyrimidin-7-one Form II. 2θ values in unit of degree in accordance with the abscissa. The intensity of diffraction peak as ordinate.

The crystal Form II of 6-Acetyl-8-cyclopentyl-5-methyl-2-(5-piperazin-1-yl-pyridin-2-ylamino)-8H-pyrido[2,3-d]pyrimidin-7-one was obtained after slurring of 1.0 g of 6-Acetyl-8-cyclopentyl-5-methyl-2-(5-piperazin-1-yl-pyridin-2-ylamino)-8H-pyrido[2,3-d]pyrimidin-7-one in 50 ml of ethyl Formate for 24 hours. The XRPD pattern of the resulting crystal Form II is shown in FIG. 2 and information of diffraction peaks at 2θ values are listed in the following table:

| 2θ (degree) | d (Å) | I (Height) % |
|---|---|---|
| 7.602 | 11.6204 | 28.5 |
| 8.517 | 10.3736 | 6.1 |
| 8.901 | 9.9266 | 24.3 |
| 9.561 | 9.2431 | 74.3 |
| 11.42 | 7.7421 | 71 |
| 12.14 | 7.2846 | 51.2 |
| 13.02 | 6.7939 | 23.8 |
| 13.441 | 6.582 | 7.5 |
| 14.438 | 6.1297 | 9.9 |
| 15.34 | 5.7713 | 20.4 |
| 16.261 | 5.4466 | 11.6 |
| 16.74 | 5.2917 | 39.7 |
| 17.26 | 5.1333 | 19.9 |
| 19.22 | 4.614 | 100 |
| 19.599 | 4.5257 | 19 |
| 20.738 | 4.2797 | 8.7 |
| 21.74 | 4.0846 | 33 |
| 22.479 | 3.952 | 57.1 |
| 23.82 | 3.7325 | 14.5 |
| 26.479 | 3.3634 | 11 |
| 27.182 | 3.2779 | 12.1 |
| 28.44 | 3.1357 | 10.4 |

Figure 15:
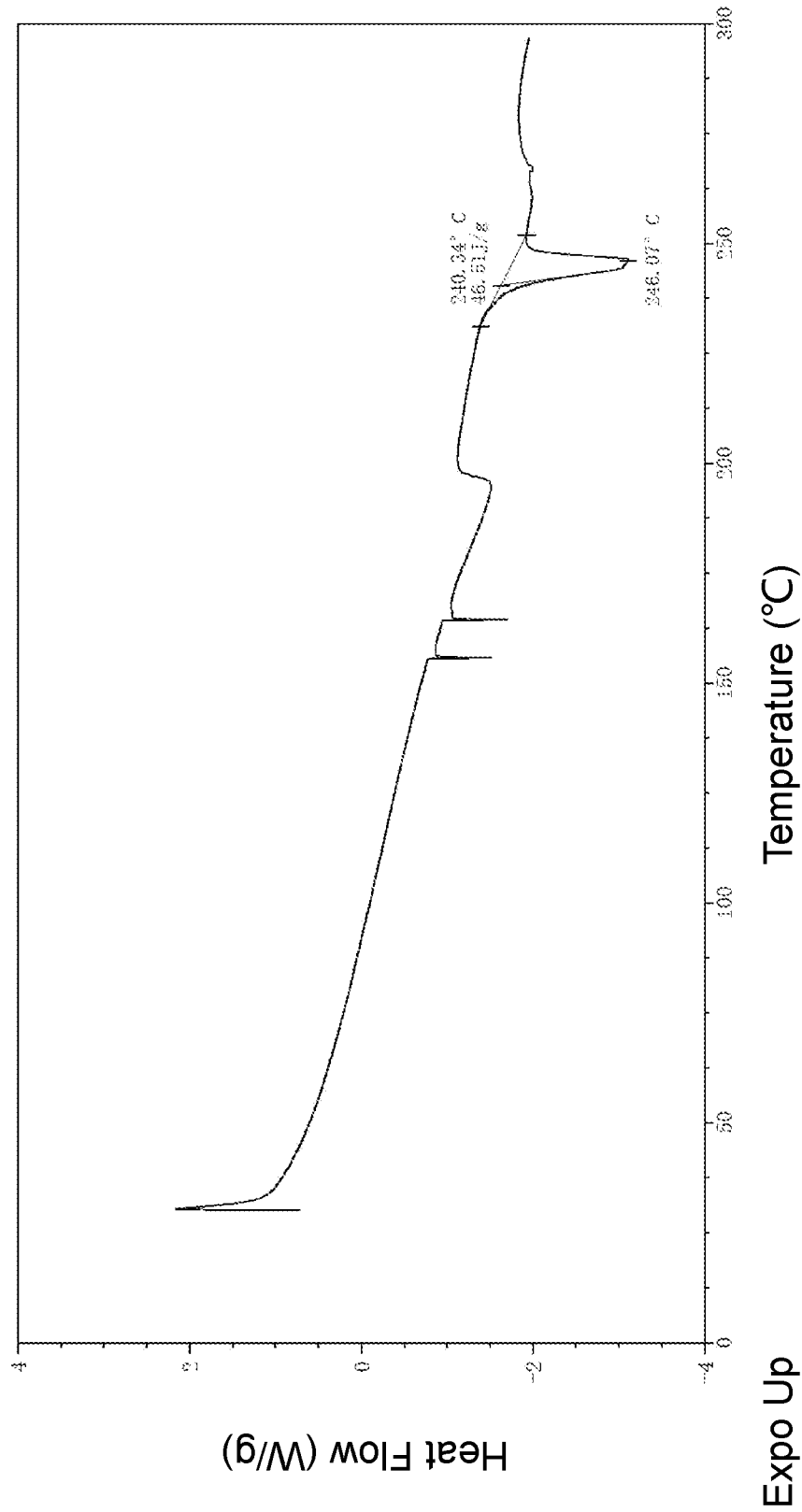
FIG. 15 is a DSC plot of 6-Acetyl-8-cyclopentyl-5-methyl-2-(5-piperazin-1-yl-pyridin-2-ylamino)-8H-pyrido[2,3-d]pyrimidin-7-one Form II. Temperature in unit of 0 C in accordance with the abscissa. The Heat flow (w/g) as ordinate.

A differential scanning calorimetry (DSC) analysis was performed on the crystal Form II in Example 2, using a TA Q2000 differential scanning calorimeter using an $N_2$ atmosphere at a temperature rising rate of 10° C./min. The DSC plot of Form II is shown in FIG. 15.

The thermogravimetric (TGA) analysis of the crystal Form II in Example 2 was carried out using a TA Q500 thermogravimetric analyzer using a $N_2$ atmosphere at a heating rate of 10° C./min. The TGA plot of Form II is shown in FIG. 26.

Example 3

The crystal From III of 6-Acetyl-8-cyclopentyl-5-methyl-2-(5-piperazin-1-yl-pyridin-2-ylamino)-8H-pyrido[2,3-d]pyrimidin-7-one was precipitated out after dissolving of 10 milligrams (mg) of 6-Acetyl-8-cyclopentyl-5-methyl-2-(5-piperazin-1-yl-pyridin-2-ylamino)-8H-pyrido[2,3-d]pyrimidin-7-one in 120 microliter Formic acid following by slowly adding 1 mL of isopropyl acetate.

Figure 3:
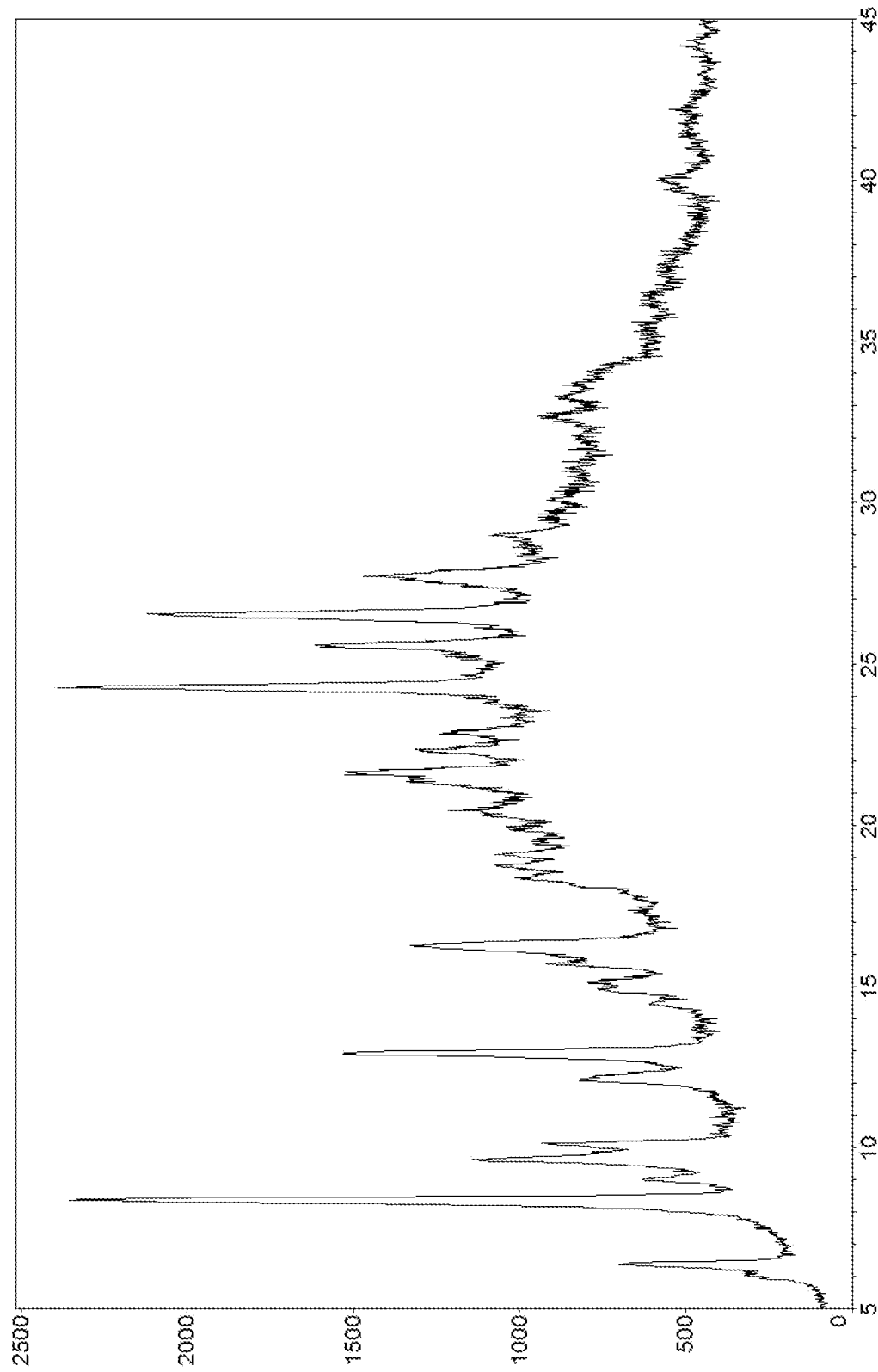
FIG. 3 is an XRPD pattern of 6-Acetyl-8-cyclopentyl-5-methyl-2-(5-piperazin-1-yl-pyridin-2-ylamino)-8H-pyrido[2,3-d]pyrimidin-7-one Form III. 2θ values in unit of degree in accordance with the abscissa. The intensity of diffraction peak as ordinate.

The XRPD pattern of the resulting crystal Form III is shown in FIG. 3 and information of diffraction peaks at 2θ values are listed in the following table:

| 2θ (degree) | d (Å) | I (Height) % |
|---|---|---|
| 6.401 | 13.797 | 30 |
| 8.401 | 10.5165 | 100 |
| 9.021 | 9.7953 | 9.5 |
| 9.64 | 9.1673 | 37.6 |
| 10.138 | 8.7182 | 25.6 |
| 12.102 | 7.3075 | 16.7 |
| 12.922 | 6.8454 | 53.1 |
| 14.45 | 6.1248 | 3.3 |
| 14.938 | 5.9257 | 11 |
| 15.158 | 5.8403 | 11.2 |
| 15.703 | 5.6387 | 16.6 |
| 16.28 | 5.4402 | 37 |
| 18.36 | 4.8283 | 14.2 |
| 18.758 | 4.7268 | 13.8 |
| 19.102 | 4.6423 | 10 |
| 19.943 | 4.4484 | 5.1 |
| 20.48 | 4.333 | 11.8 |
| 21.381 | 4.1524 | 16.2 |
| 21.657 | 4.1 | 25.2 |
| 22.355 | 3.9737 | 14.7 |
| 22.844 | 3.8896 | 12.2 |
| 24.28 | 3.6627 | 68.5 |
| 25.58 | 3.4795 | 28.3 |
| 26.558 | 3.3535 | 55.3 |
| 27.74 | 3.2133 | 24.9 |
| 29.002 | 3.0762 | 9.2 |
| 32.679 | 2.738 | 7.7 |

Figure 16:
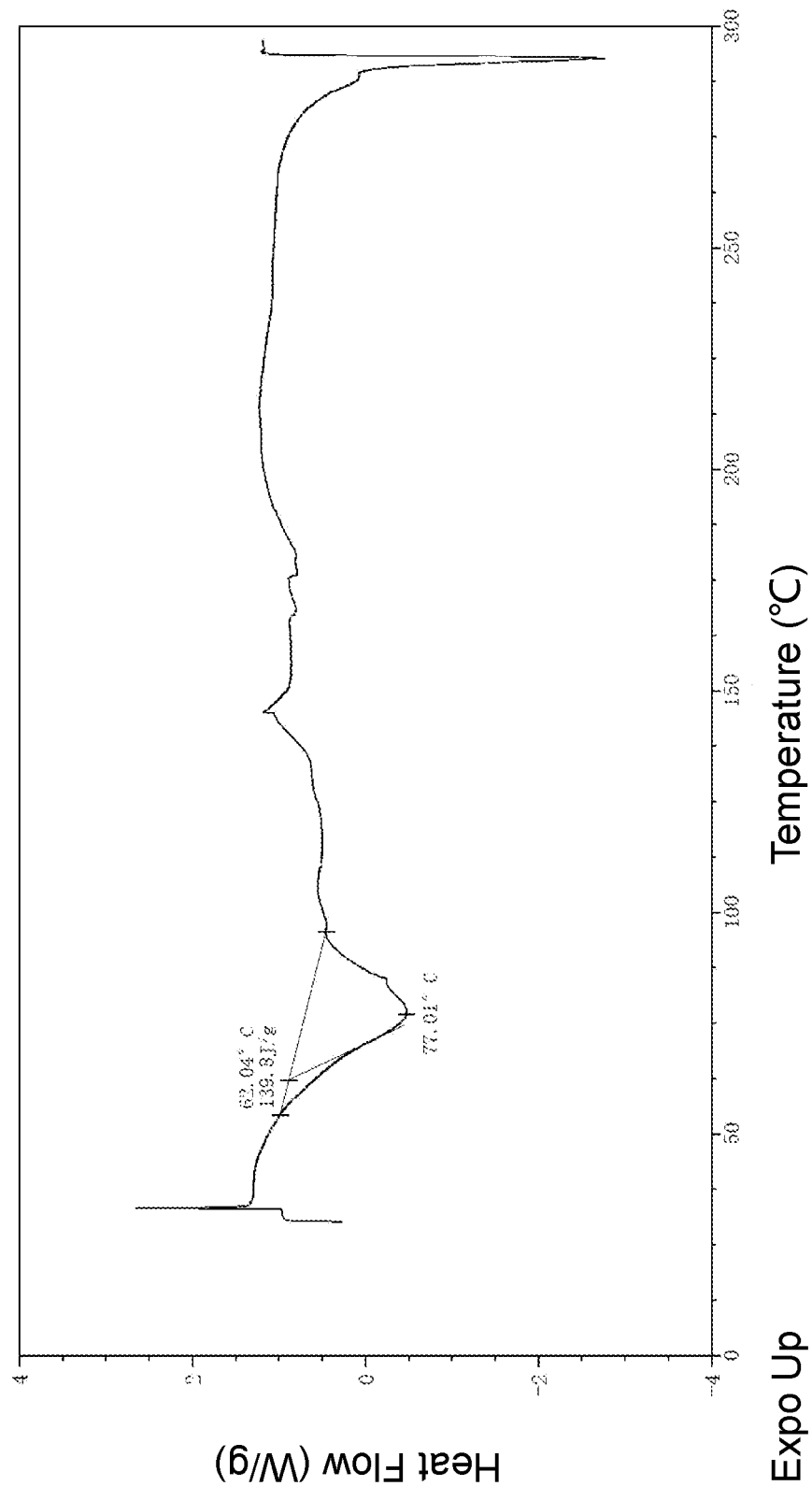
FIG. 16 is a DSC plot of 6-Acetyl-8-cyclopentyl-5-methyl-2-(5-piperazin-1-yl-pyridin-2-ylamino)-8H-pyrido[2,3-d]pyrimidin-7-one Form III. Temperature in unit of 0 C in accordance with the abscissa. The Heat flow (w/g) as ordinate.

A differential scanning calorimetry (DSC) analysis was performed on the crystal Form III in Example 3, using a TA Q2000 differential scanning calorimeter using an $N_2$ atmosphere at a temperature rising rate of 10° C./min. The DSC plot of Form III is shown in FIG. 16.

The thermogravimetric (TGA) analysis of the crystal Form III in Example 3 was carried out using a TA Q500 thermogravimetric analyzer using a $N_2$ atmosphere at a heating rate of 10° C./min. The TGA plot of Form III is shown in FIG. 27.

Example 4

The crystal From IV of 6-Acetyl-8-cyclopentyl-5-methyl-2-(5-piperazin-1-yl-pyridin-2-ylamino)-8H-pyrido[2,3-d]pyrimidin-7-one was precipitated out after dissolving of 10 mg of 6-Acetyl-8-cyclopentyl-5-methyl-2-(5-piperazin-1-yl-pyridin-2-ylamino)-8H-pyrido[2,3-d]pyrimidin-7-one in 120 microliter acetic acid following by slowly adding 1 mL of isopropyl acetate.

Figure 4:
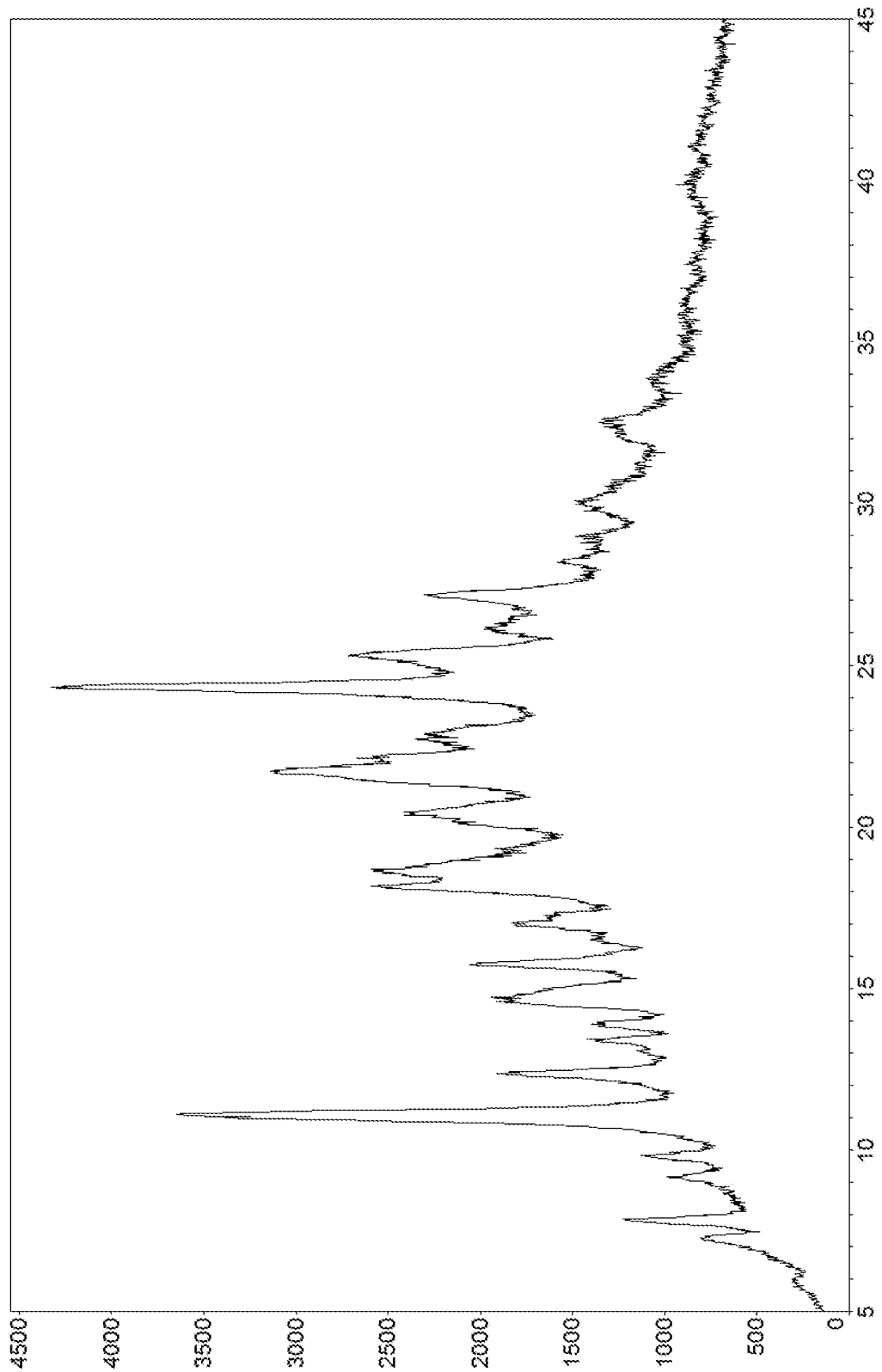
FIG. 4 is an XRPD pattern of 6-Acetyl-8-cyclopentyl-5-methyl-2-(5-piperazin-1-yl-pyridin-2-ylamino)-8H-pyrido[2,3-d]pyrimidin-7-one Form IV. 2θ values in unit of degree in accordance with the abscissa. The intensity of diffraction peak as ordinate.

The XRPD pattern of the resulting crystal Form IV is shown in FIG. 4 and information of diffraction peaks at 2θ values are listed in the following table:

| 2θ (degree) | d (Å) | I (Height) % |
|---|---|---|
| 7.299 | 12.1006 | 19.8 |
| 7.878 | 11.2135 | 24.5 |
| 9.178 | 9.6279 | 10.5 |
| 9.839 | 8.9826 | 13.5 |
| 11.12 | 7.9504 | 100 |
| 12.399 | 7.1326 | 32.6 |
| 13.437 | 6.5841 | 13.5 |
| 13.92 | 6.3566 | 12.2 |
| 14.601 | 6.0617 | 27.6 |
| 15.742 | 5.625 | 31.3 |
| 16.52 | 5.3616 | 7 |
| 17.04 | 5.1992 | 19.2 |
| 18.16 | 4.8808 | 35.8 |
| 18.698 | 4.7417 | 38.7 |
| 20.382 | 4.3535 | 26.2 |
| 21.74 | 4.0847 | 42.8 |
| 22.14 | 4.0117 | 26.5 |
| 22.704 | 3.9133 | 12 |
| 24.321 | 3.6567 | 83.4 |
| 25.301 | 3.5171 | 27.4 |
| 26.124 | 3.4083 | 9.4 |
| 27.18 | 3.2782 | 25.2 |
| 28.2 | 3.1618 | 7.2 |
| 30.077 | 2.9687 | 11.7 |
| 32.621 | 2.7427 | 11.3 |

Figure 17:
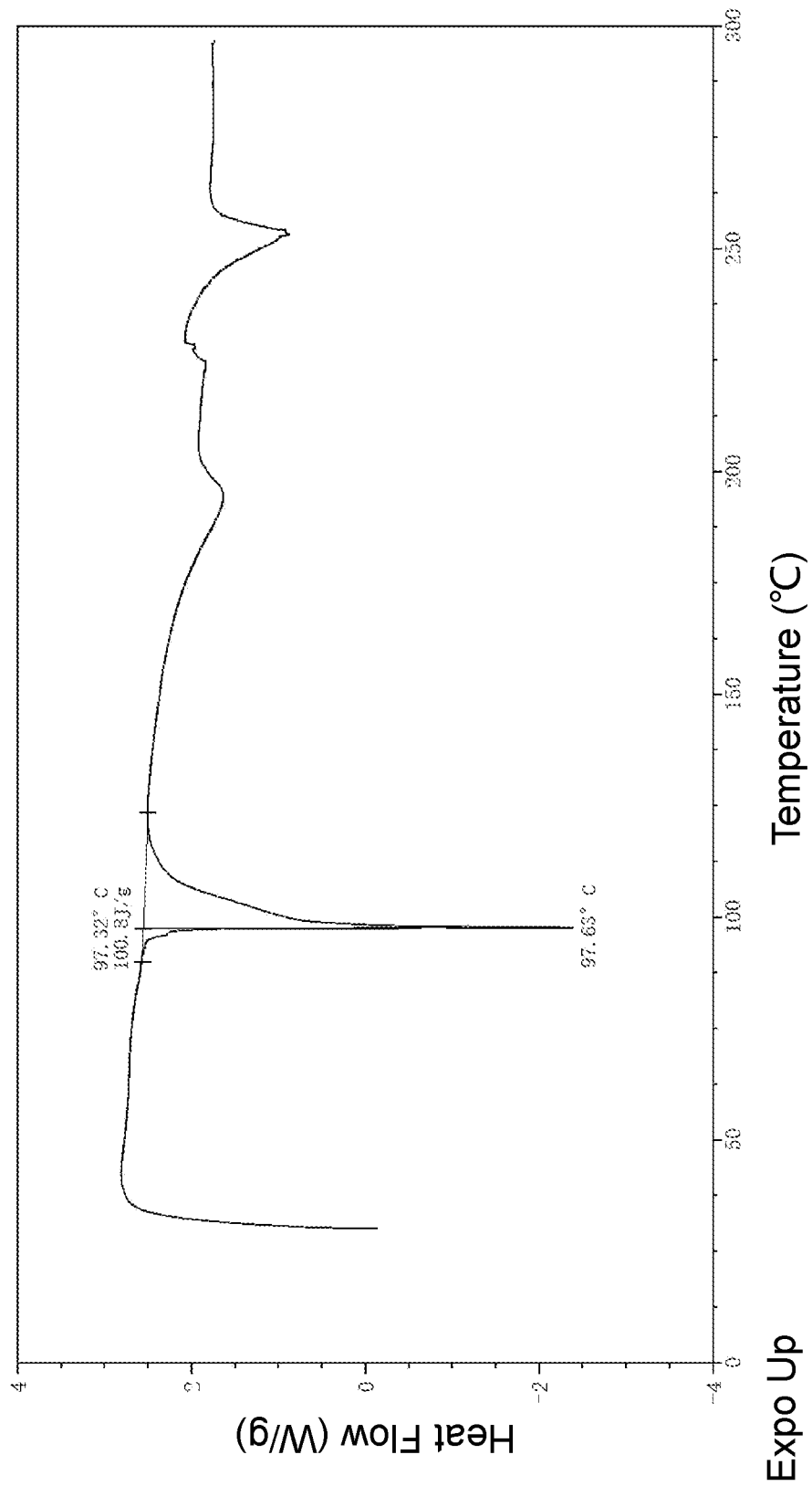
FIG. 17 is a DSC plot of 6-Acetyl-8-cyclopentyl-5-methyl-2-(5-piperazin-1-yl-pyridin-2-ylamino)-8H-pyrido[2,3-d]pyrimidin-7-one Form IV. Temperature in unit of 0 C in accordance with the abscissa. The Heat flow (w/g) as ordinate.

A differential scanning calorimetry (DSC) analysis was performed on the crystal Form IV in Example 4, using a TA Q2000 differential scanning calorimeter using an N₂ atmosphere at a temperature rising rate of 10° C./min. The DSC plot of Form IV is shown in FIG. 17.

The thermogravimetric (TGA) analysis of the crystal Form IV in Example 4 was carried out using a TA Q500 thermogravimetric analyzer using a N₂ atmosphere at a heating rate of 10° C./min. The TGA plot of Form IV is shown in FIG. 28.

Example 5

1.0 g of 6-Acetyl-8-cyclopentyl-5-methyl-2-(5-piperazin-1-yl-pyridin-2-ylamino)-8H-pyrido[2,3-d]pyrimidin-7-one was dissolved in 10 mL of chloroform and then N-butanol was added drop wise until the solution became turbid. The suspension was allowed to be stirred overnight. The crystal Form V was obtained after the filtration.

Figure 5:
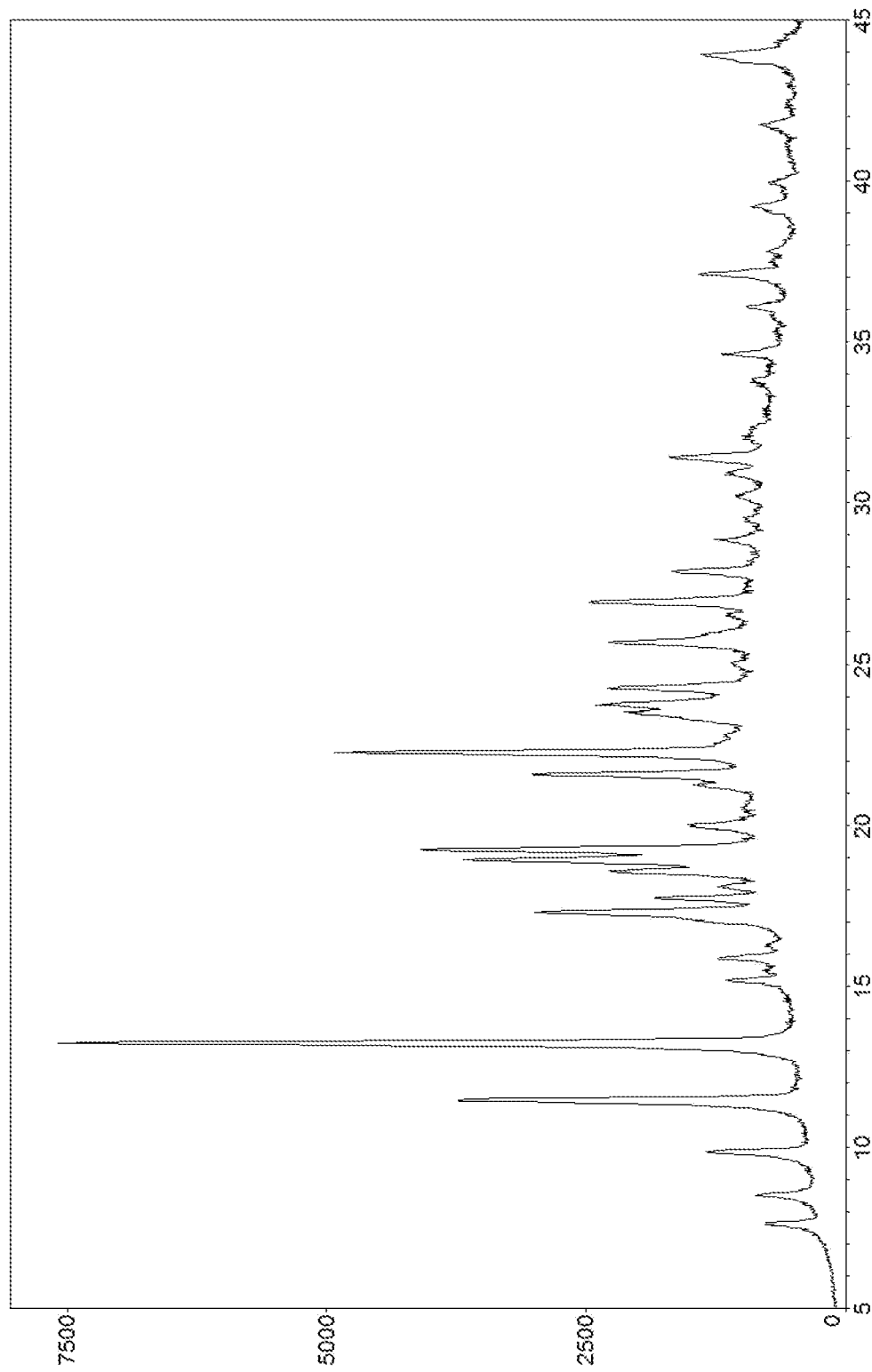
FIG. 5 is an XRPD pattern of 6-Acetyl-8-cyclopentyl-5-methyl-2-(5-piperazin-1-yl-pyridin-2-ylamino)-8H-pyrido[2,3-d]pyrimidin-7-one Form V. 2θ values in unit of degree in accordance with the abscissa. The intensity of diffraction peak as ordinate.

The XRPD pattern of the resulting crystal Form V is shown in FIG. 5 and information of diffraction peaks at 2θ values are listed in the following table:

| 2θ (degree) | d (Å) | I (Height) % |
|---|---|---|
| 7.642 | 11.5596 | 7.2 |
| 8.524 | 10.3653 | 7.9 |
| 9.898 | 8.9292 | 13.8 |
| 11.499 | 7.6892 | 46.5 |
| 13.26 | 6.6715 | 100 |
| 15.2 | 5.8241 | 7.8 |
| 15.882 | 5.5756 | 8.3 |
| 17.319 | 5.116 | 30.8 |
| 17.741 | 4.9952 | 13.1 |
| 18.118 | 4.8922 | 4 |
| 18.598 | 4.7669 | 19 |
| 18.94 | 4.6817 | 38.8 |
| 19.261 | 4.6045 | 44.6 |
| 20.037 | 4.4278 | 8.4 |
| 21.243 | 4.1791 | 5.5 |
| 21.597 | 4.1113 | 27.5 |
| 22.279 | 3.987 | 53.9 |
| 23.519 | 3.7795 | 14.9 |
| 23.741 | 3.7446 | 19.3 |
| 24.262 | 3.6654 | 15.1 |
| 25.699 | 3.4636 | 18.3 |
| 26.939 | 3.3069 | 21.1 |
| 27.899 | 3.1953 | 10.7 |
| 28.879 | 3.089 | 5.7 |
| 29.539 | 3.0215 | 2.1 |
| 30.257 | 2.9515 | 3.3 |
| 30.902 | 2.8913 | 4.6 |
| 31.439 | 2.8431 | 12.2 |
| 33.857 | 2.6454 | 2.6 |
| 34.639 | 2.5875 | 7.1 |
| 36.1 | 2.486 | 5 |
| 37.119 | 2.4201 | 11.6 |
| 39.201 | 2.2962 | 5.8 |
| 39.957 | 2.2545 | 3 |
| 41.722 | 2.1631 | 4.5 |
| 43.919 | 2.0599 | 12.8 |

Figure 18:
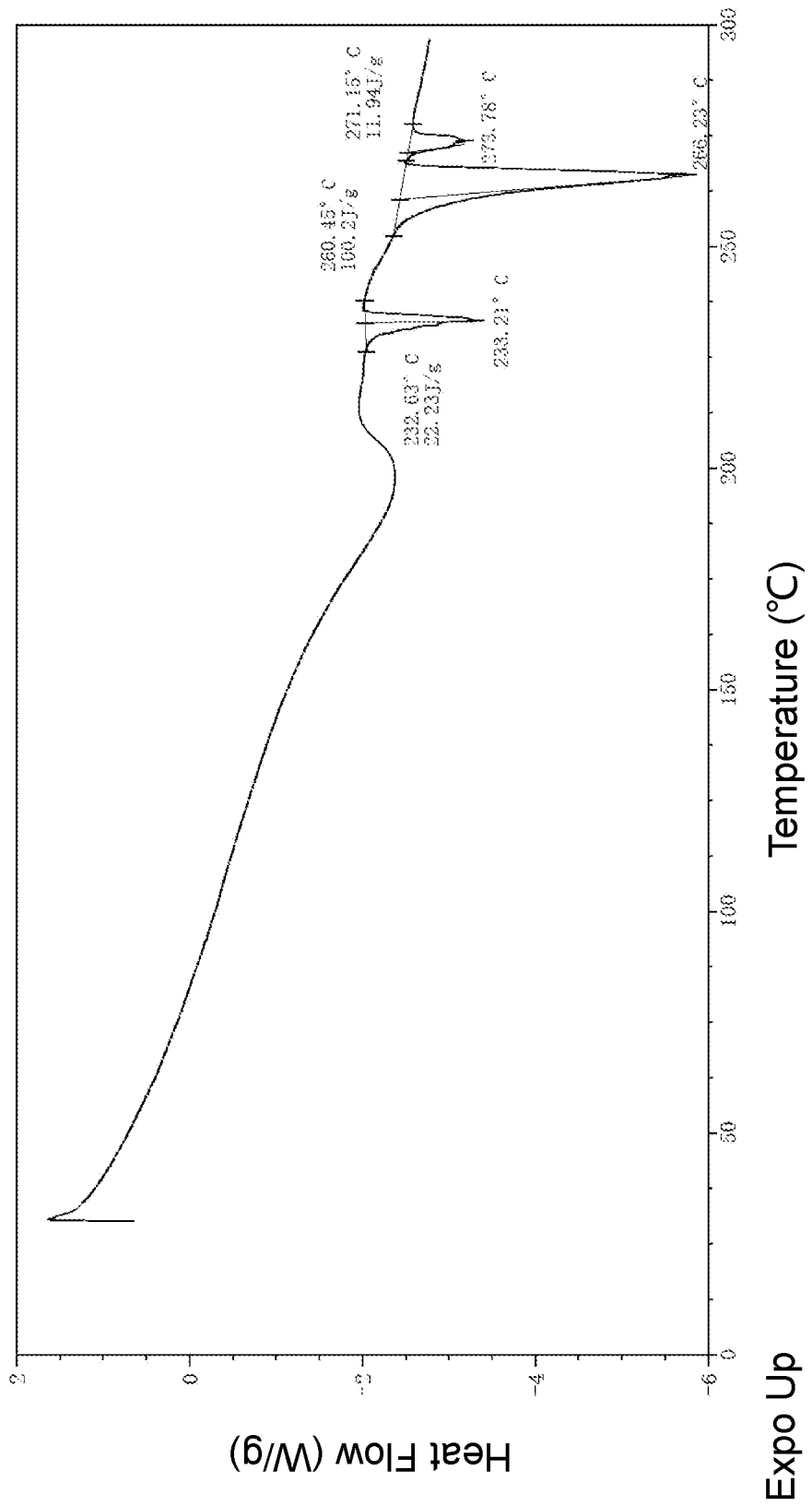
FIG. 18 is a DSC plot of 6-Acetyl-8-cyclopentyl-5-methyl-2-(5-piperazin-1-yl-pyridin-2-ylamino)-8H-pyrido[2,3-d]pyrimidin-7-one Form V. Temperature in unit of 0 C in accordance with the abscissa. The Heat flow (w/g) as ordinate.

A differential scanning calorimetry (DSC) analysis was performed on the crystal Form V in Example 5, using a TA Q2000 differential scanning calorimeter using an N₂ atmosphere at a temperature rising rate of 10° C./min. The DSC plot of Form V is shown in FIG. 18.

The thermogravimetric (TGA) analysis of the crystal Form V in Example 5 was carried out using a TA Q500 thermogravimetric analyzer using a N₂ atmosphere at a heating rate of 10° C./min. The TGA plot of Form V is shown in FIG. 29.

Example 6

1.0 g of 6-Acetyl-8-cyclopentyl-5-methyl-2-(5-piperazin-1-yl-pyridin-2-ylamino)-8H-pyrido[2,3-d]pyrimidin-7-one was dissolved in 10 mL of chloroform and then N-butyl ether was added drop wise until the solution became turbid. The suspension was allowed to be stirred overnight. The crystal Form VI was obtained after the filtration.

Figure 6:
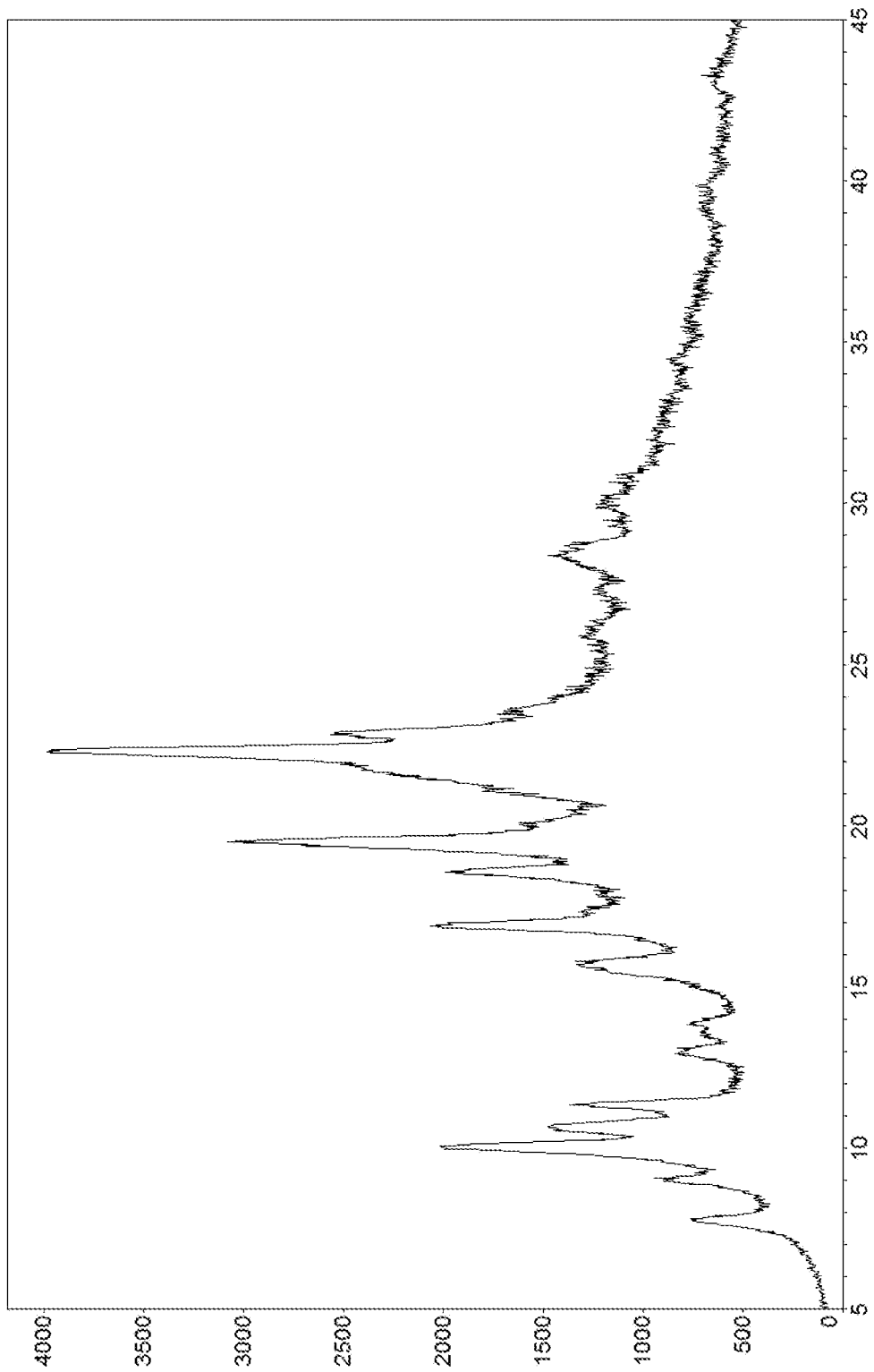
FIG. 6 is an XRPD pattern of 6-Acetyl-8-cyclopentyl-5-methyl-2-(5-piperazin-1-yl-pyridin-2-ylamino)-8H-pyrido[2,3-d]pyrimidin-7-one Form VI. 2θ values in unit of degree in accordance with the abscissa. The intensity of diffraction peak as ordinate.

The XRPD pattern of the resulting crystal Form VI is shown in FIG. 6 and information of diffraction peaks at 2θ values are listed in the following table:

| 2θ (degree) | d (Å) | I (Height) % |
|---|---|---|
| 7.819 | 11.2975 | 25.2 |
| 9.078 | 9.7334 | 14.7 |
| 10.079 | 8.7687 | 55 |
| 10.681 | 8.2763 | 29.3 |
| 11.361 | 7.7819 | 24.8 |
| 12.96 | 6.8252 | 11.5 |
| 13.92 | 6.3566 | 8 |
| 15.8 | 5.6045 | 24.2 |
| 16.919 | 5.236 | 47.9 |
| 18.58 | 4.7716 | 27.1 |
| 19.519 | 4.544 | 75.5 |
| 22.301 | 3.9832 | 100 |
| 22.901 | 3.8802 | 17.1 |
| 28.364 | 3.144 | 14.5 |

Figure 19:
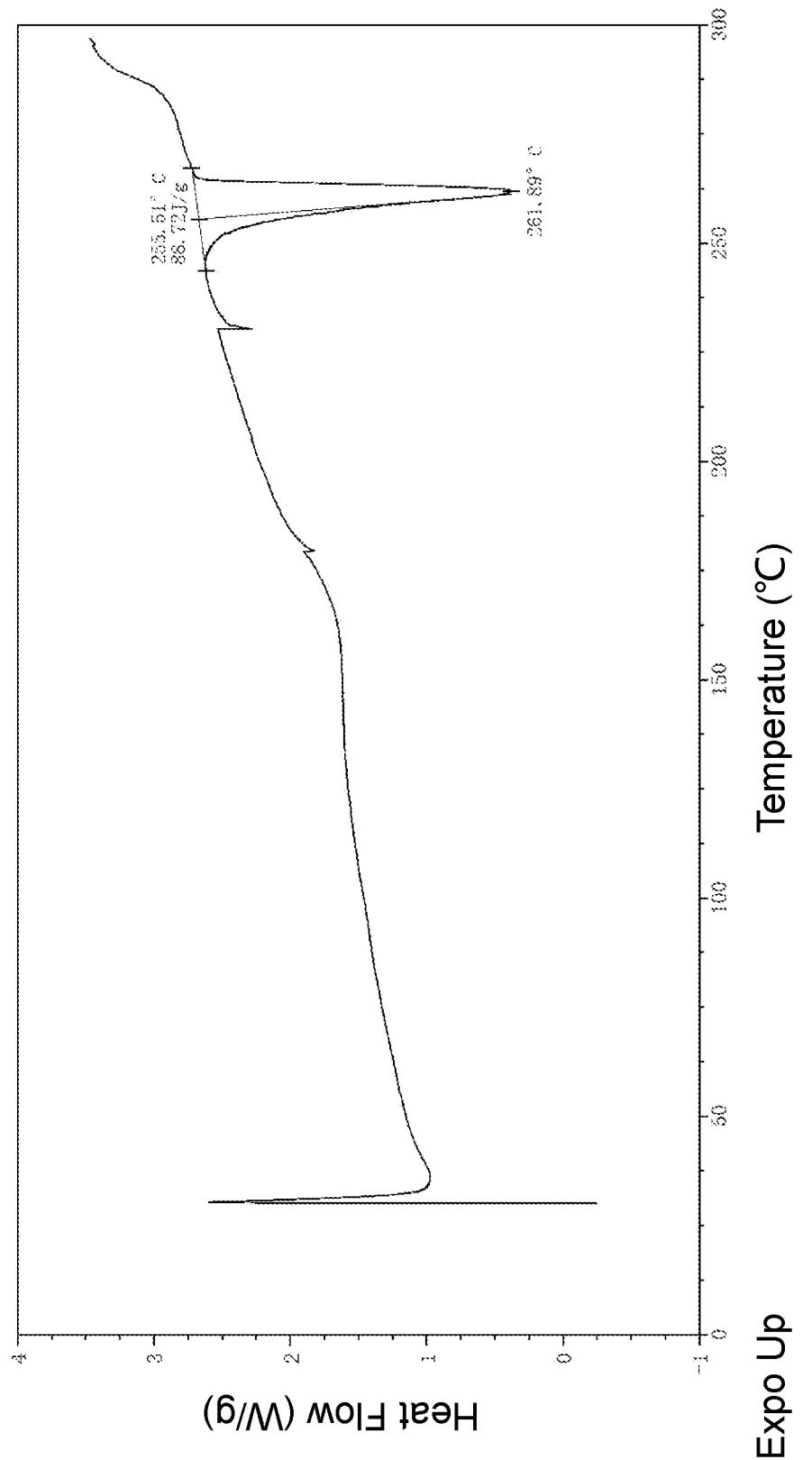
FIG. 19 is a DSC plot of 6-Acetyl-8-cyclopentyl-5-methyl-2-(5-piperazin-1-yl-pyridin-2-ylamino)-8H-pyrido[2,3-d]pyrimidin-7-one Form VI. Temperature in unit of 0 C in accordance with the abscissa. The Heat flow (w/g) as ordinate.

A differential scanning calorimetry (DSC) analysis was performed on the crystal Form VI in Example 6, using a TA Q2000 differential scanning calorimeter using an N₂ atmosphere at a temperature rising rate of 10° C./min. The DSC plot of Form VI is shown in FIG. 19.

The thermogravimetric (TGA) analysis of the crystal Form VI in Example 6 was carried out using a TA Q500 thermogravimetric analyzer using a N₂ atmosphere at a heating rate of 10° C./min. The TGA plot of Form VI is shown in FIG. 30.

Example 7

1.0 g of 6-Acetyl-8-cyclopentyl-5-methyl-2-(5-piperazin-1-yl-pyridin-2-ylamino)-8H-pyrido[2,3-d]pyrimidin-7-one was dissolved in 10 mL of chloroform and then 3-pentanone was added drop wise until the solution became turbid. The suspension was allowed to be stirred overnight. The crystal Form VII was obtained after the filtration.

Figure 7:
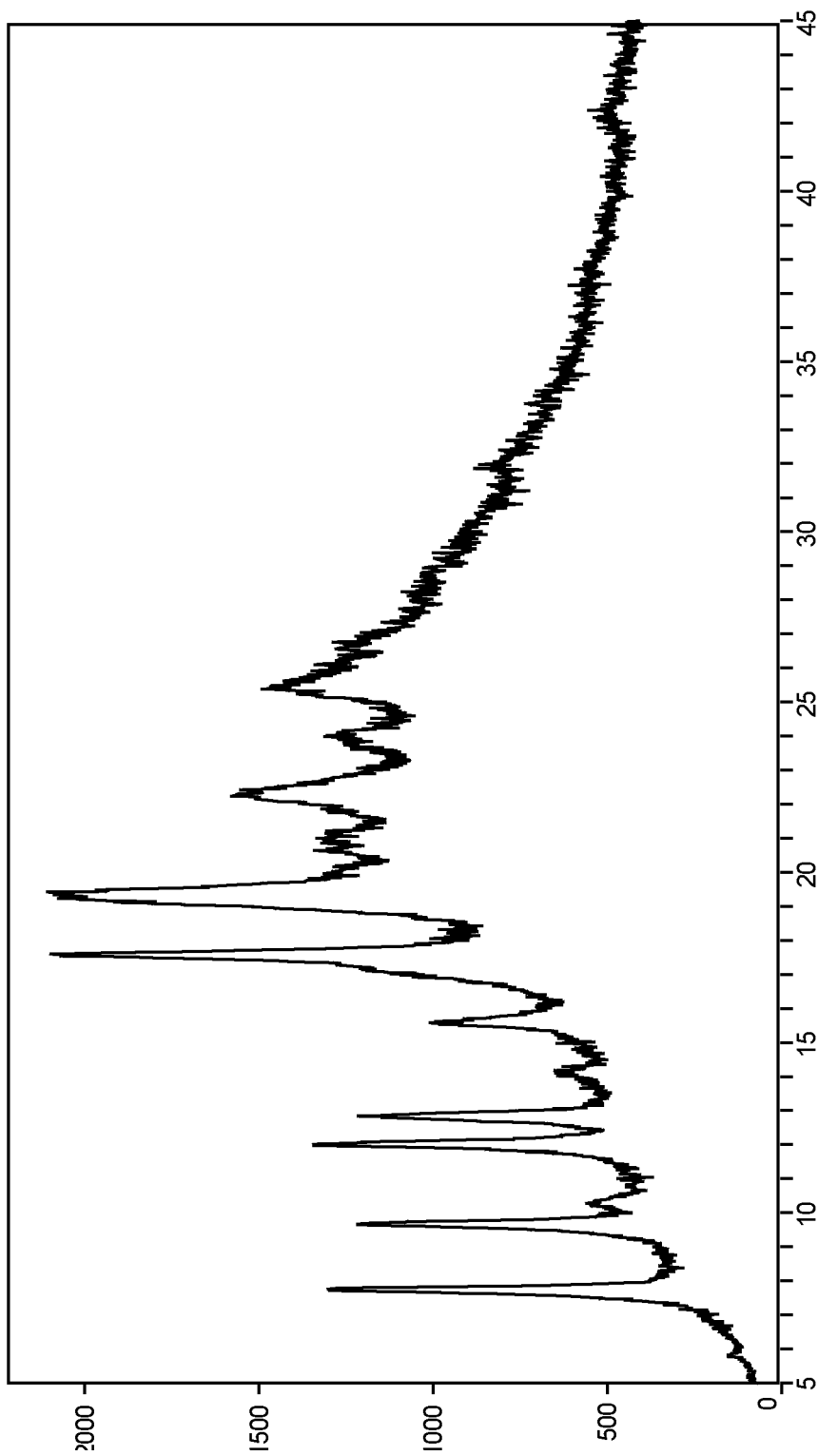
FIG. 7 is an XRPD pattern of 6-Acetyl-8-cyclopentyl-5-methyl-2-(5-piperazin-1-yl-pyridin-2-ylamino)-8H-pyrido[2,3-d]pyrimidin-7-one Form VII. 2θ values in unit of degree in accordance with the abscissa. The intensity of diffraction peak as ordinate.

The XRPD pattern of the resulting crystal Form VII is shown in FIG. 7 and information of diffraction peaks at 2θ values was listed in the following table:

| 2θ (degree) | d (Å) | I (Height) % |
|---|---|---|
| 7.759 | 11.3845 | 83 |
| 9.661 | 9.1477 | 67.5 |
| 10.28 | 8.5975 | 7.4 |
| 11.982 | 7.3799 | 67.4 |
| 12.84 | 6.8891 | 55 |
| 14.174 | 6.2435 | 9.9 |
| 15.579 | 5.6832 | 31.4 |
| 17.14 | 5.1691 | 33.6 |
| 17.599 | 5.0353 | 100 |
| 19.419 | 4.5674 | 85.1 |
| 22.242 | 3.9936 | 34.7 |
| 24.015 | 3.7026 | 16.2 |
| 25.459 | 3.4958 | 26.2 |

Example 8

One grain (g) of 6-Acetyl-8-cyclopentyl-5-methyl-2-(5-piperazin-1-yl-pyridin-2-ylamino)-8H-pyrido[2,3-d]pyrimidin-7-one was dissolved in 10 mL of trifluoroethanol in a glass bottle. Place the glass bottle with the solution inside into an ultra-sonication water bath. The water was added drop wise with the ultra-sonication on until the solution became turbid. The suspension was kept in the ultra-sonication field for 2 hours. The crystal Form VIII was obtained after filtration.

Figure 8:
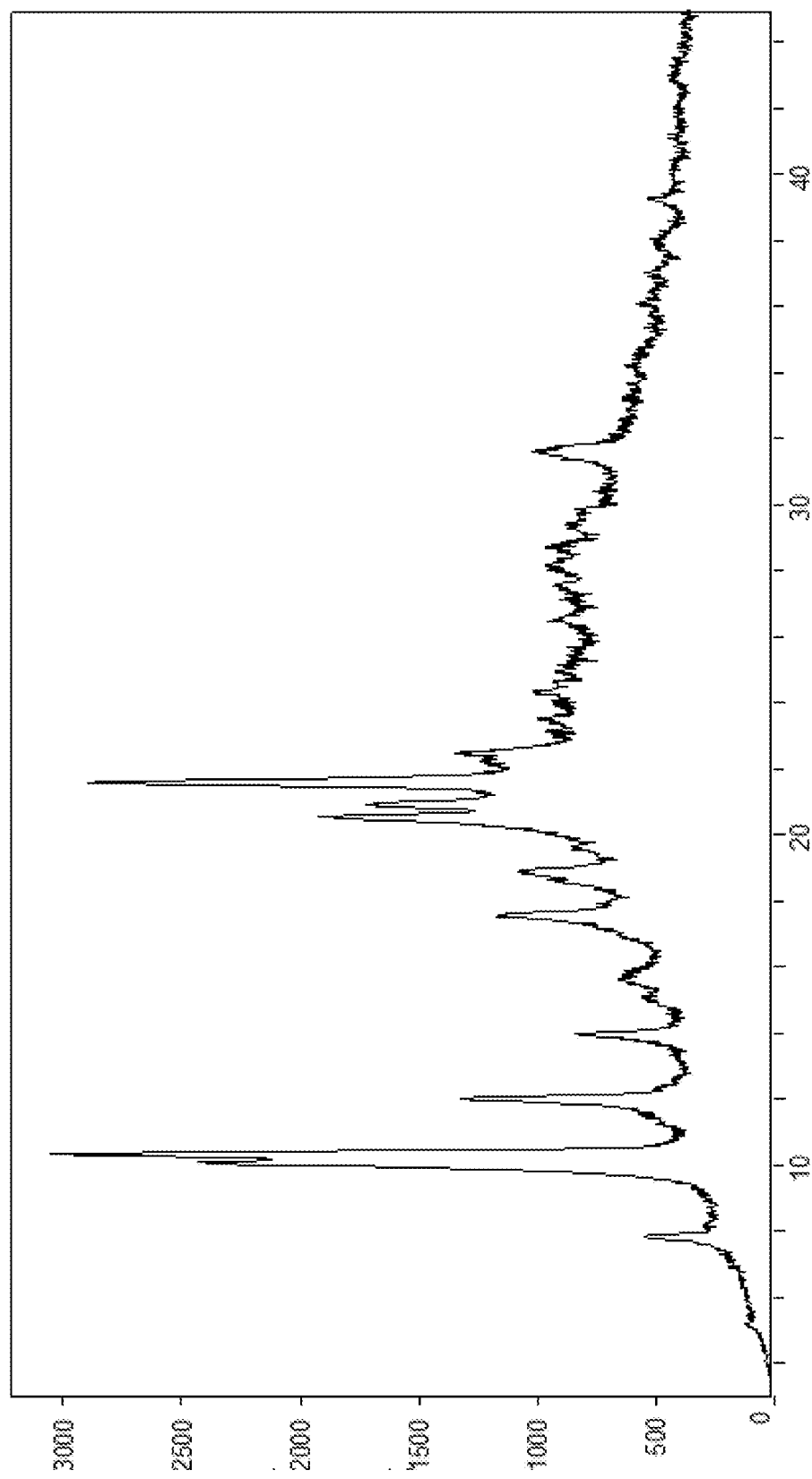
FIG. 8 is an XRPD pattern of 6-Acetyl-8-cyclopentyl-5-methyl-2-(5-piperazin-1-yl-pyridin-2-ylamino)-8H-pyrido[2,3-d]pyrimidin-7-one Form VIII. 2θ values in unit of degree in accordance with the abscissa. The intensity of diffraction peak as ordinate.

The XRPD pattern of the resulting crystal Form VIII is shown in FIG. 8 and information of diffraction peaks at 2θ values was listed in the following table:

| 2θ (degree) | d (Å) | I (Height) % |
|---|---|---|
| 5.181 | 17.0436 | 3.4 |
| 7.839 | 11.2687 | 12.2 |
| 10.041 | 8.8021 | 76.2 |
| 10.32 | 8.5649 | 100 |
| 12 | 7.369 | 34.8 |
| 13.959 | 6.3392 | 16.5 |
| 15.619 | 5.669 | 7.4 |
| 17.521 | 5.0575 | 21.3 |
| 18.582 | 4.771 | 8.8 |
| 18.9 | 4.6916 | 14.4 |
| 20.539 | 4.3206 | 33.5 |
| 20.919 | 4.243 | 26.1 |
| 21.58 | 4.1145 | 64.2 |
| 22.481 | 3.9515 | 11.7 |
| 31.638 | 2.8256 | 13.1 |

Figure 20:
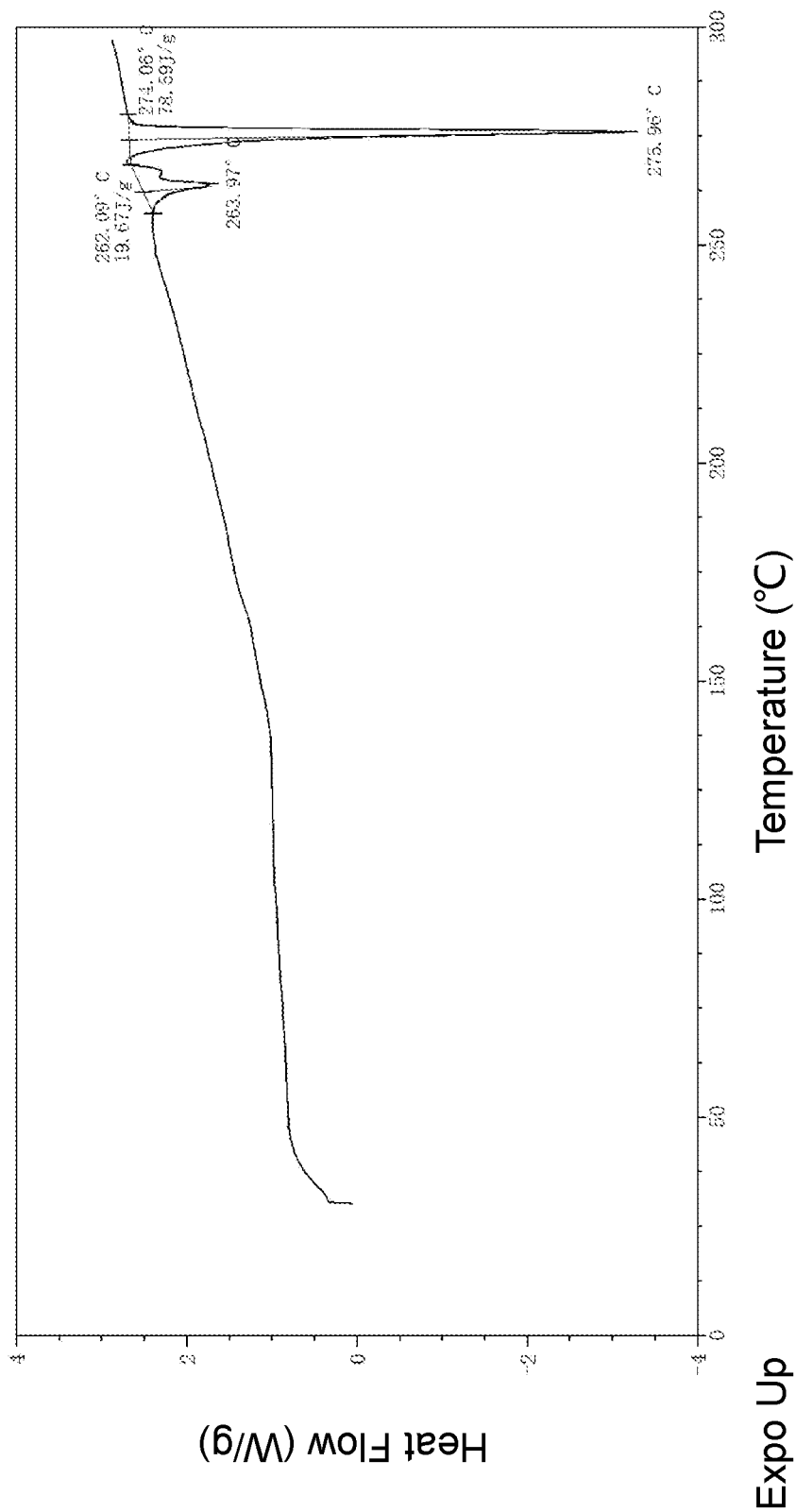
FIG. 20 is a DSC plot of 6-Acetyl-8-cyclopentyl-5-methyl-2-(5-piperazin-1-yl-pyridin-2-ylamino)-8H-pyrido[2,3-d]pyrimidin-7-one Form VIII. Temperature in unit of 0 C in accordance with the abscissa. The Heat flow (w/g) as ordinate.

A differential scanning calorimetry (DSC) analysis was performed on the crystal Form VIII in Example 8, using a TA Q2000 differential scanning calorimeter using an $N_2$ atmosphere at a temperature rising rate of 10° C./min. The DSC plot of Form VIII is shown in FIG. 20.

The thermogravimetric (TGA) analysis of the crystal Form VIII in Example 8 was carried out using a TA Q500 thermogravimetric analyzer using a $N_2$ atmosphere at a heating rate of 10° C./min. The TGA plot of Form VIII is shown in FIG. 31.

Example 9

Two hundred (200) milligrams (mg) of 6-Acetyl-8-cyclopentyl-5-methyl-2-(5-piperazin-1-yl-pyridin-2-ylamino)-8H-pyrido[2,3-d]pyrimidin-7-one was dissolved in trifluoroethanol and then isopropyl ether was added drop wise until the solution became turbid. The suspension was allowed to be stirred overnight. The crystal Form IX was obtained after the filtration.

Figure 9:
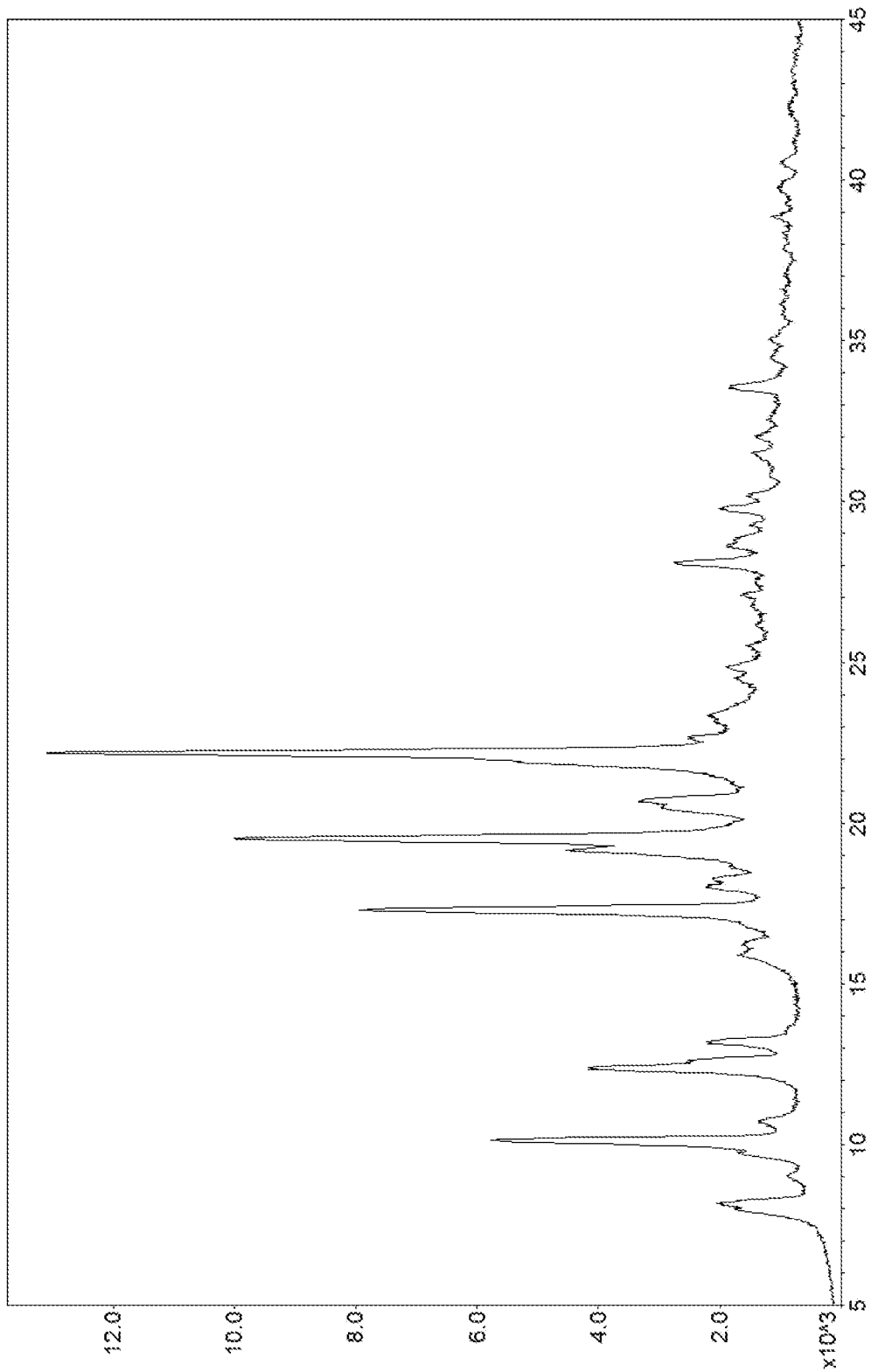
FIG. 9 is an XRPD pattern of 6-Acetyl-8-cyclopentyl-5-methyl-2-(5-piperazin-1-yl-pyridin-2-ylamino)-8H-pyrido[2,3-d]pyrimidin-7-one Form IX. 2θ values in unit of degree in accordance with the abscissa. The intensity of diffraction peak as ordinate.

The XRPD pattern of the resulting crystal Form IX is shown in FIG. 9 and information of diffraction peaks at 2θ values was listed in the following table:

| 2θ (degree) | d (Å) | I (Height) % |
|---|---|---|
| 8.18 | 10.7997 | 13.5 |
| 9.722 | 9.09 | 6.5 |
| 10.159 | 8.6997 | 44.7 |
| 10.758 | 8.2169 | 3.5 |
| 12.419 | 7.1212 | 29.6 |
| 13.2 | 6.7019 | 10.7 |
| 15.919 | 5.5625 | 5.6 |
| 16.221 | 5.4599 | 3.9 |
| 17.32 | 5.1159 | 58.5 |
| 18.021 | 4.9184 | 6.7 |
| 18.279 | 4.8494 | 5.3 |
| 19.161 | 4.6282 | 26.1 |
| 19.539 | 4.5394 | 74.4 |
| 20.7 | 4.2873 | 14.6 |
| 22.181 | 4.0044 | 100 |
| 28.119 | 3.1708 | 12.6 |
| 28.584 | 3.1203 | 5.3 |
| 29.781 | 2.9975 | 7.2 |
| 33.521 | 2.6711 | 7.5 |

Figure 21:
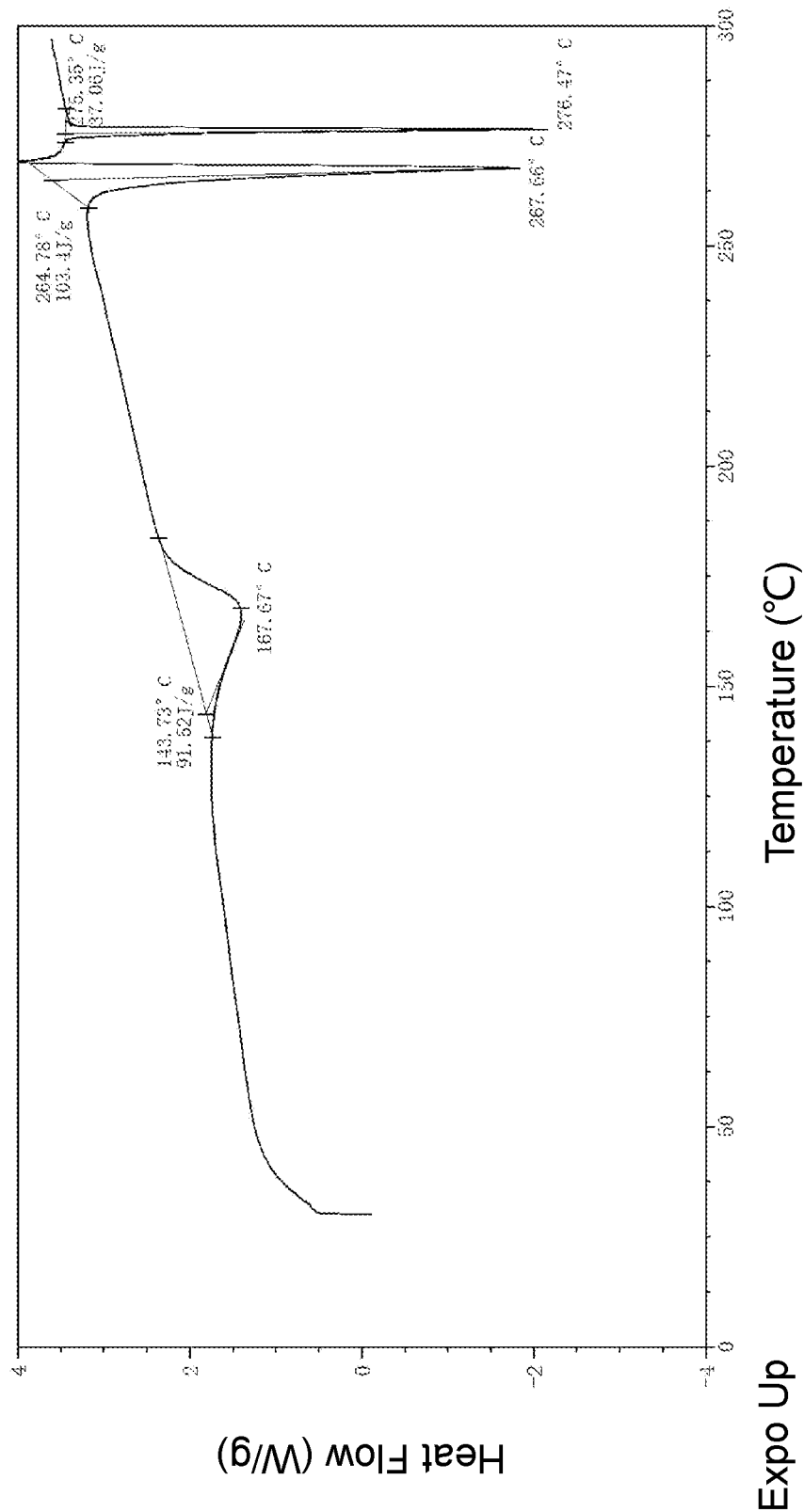
FIG. 21 is a DSC plot of 6-Acetyl-8-cyclopentyl-5-methyl-2-(5-piperazin-1-yl-pyridin-2-ylamino)-8H-pyrido[2,3-d]pyrimidin-7-one Form IX. Temperature in unit of 0 C in accordance with the abscissa. The Heat flow (w/g) as ordinate.

A differential scanning calorimetry (DSC) analysis was performed on the crystal Form IX in Example 9, using a TA Q2000 differential scanning calorimeter using an $N_2$ atmosphere at a temperature rising rate of 10° C./min. The DSC plot of Form IX is shown in FIG. 21.

The thermogravimetric (TGA) analysis of the crystal Form IX in Example 9 was carried out using a TA Q500 thermogravimetric analyzer using a $N_2$ atmosphere at a heating rate of 10° C./min. The TGA plot of Form IX is shown in FIG. 32.

Example 10

Twenty (20) mg of 6-Acetyl-8-cyclopentyl-5-methyl-2-(5-piperazin-1-yl-pyridin-2-ylamino)-8H-pyrido[2,3-d]pyrimidin-7-one was dissolved in 0.5 mL of Formic acid and then methanol was added drop wise till the solution became turbid. The crystal Form X was obtained after the filtration.

Figure 10:
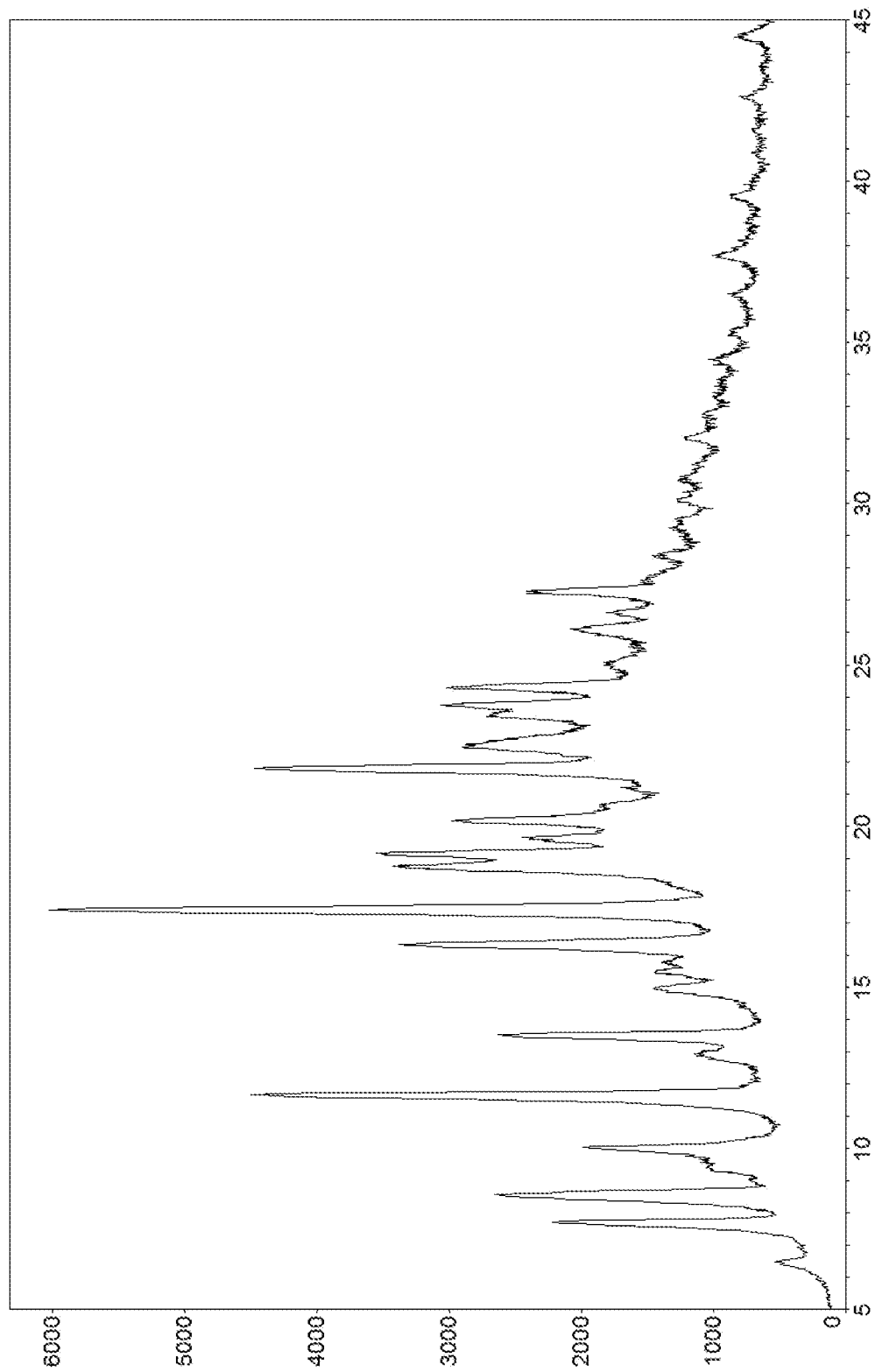
FIG. 10 is an XRPD pattern of 6-Acetyl-8-cyclopentyl-5-methyl-2-(5-piperazin-1-yl-pyridin-2-ylamino)-8H-pyrido[2,3-d]pyrimidin-7-one Form X. 2θ values in unit of degree in accordance with the abscissa. The intensity of diffraction peak as ordinate.

The XRPD pattern of the resulting crystal Form X is shown in FIG. 10 and information of diffraction peaks at 2θ values was listed in the following table:

| 2θ (degree) | d (Å) | I (Height) % |
|---|---|---|
| 6.501 | 13.5851 | 8.1 |
| 7.739 | 11.4149 | 34.6 |
| 8.58 | 10.2978 | 40.7 |
| 9.421 | 9.3797 | 7.9 |
| 10.041 | 8.802 | 28 |
| 11.699 | 7.558 | 78 |

-continued

| 2θ (degree) | d (Å) | I (Height) % |
|---|---|---|
| 12.901 | 6.8564 | 9 |
| 13.539 | 6.5345 | 39.7 |
| 14.98 | 5.9092 | 9.3 |
| 15.482 | 5.7187 | 6.8 |
| 15.781 | 5.6112 | 6.3 |
| 16.34 | 5.4203 | 46.6 |
| 17.42 | 5.0867 | 100 |
| 18.779 | 4.7215 | 36.8 |
| 19.16 | 4.6285 | 38.9 |
| 19.675 | 4.5083 | 11 |
| 20.18 | 4.3966 | 24.2 |
| 21.8 | 4.0735 | 53.2 |
| 22.479 | 3.952 | 20.2 |
| 23.403 | 3.7979 | 14.2 |
| 23.779 | 3.7388 | 24.1 |
| 24.301 | 3.6596 | 22.4 |
| 25.001 | 3.5587 | 3.9 |
| 26.139 | 3.4064 | 11.1 |
| 26.622 | 3.3455 | 5.2 |
| 27.3 | 3.264 | 20.1 |

Figure 22:
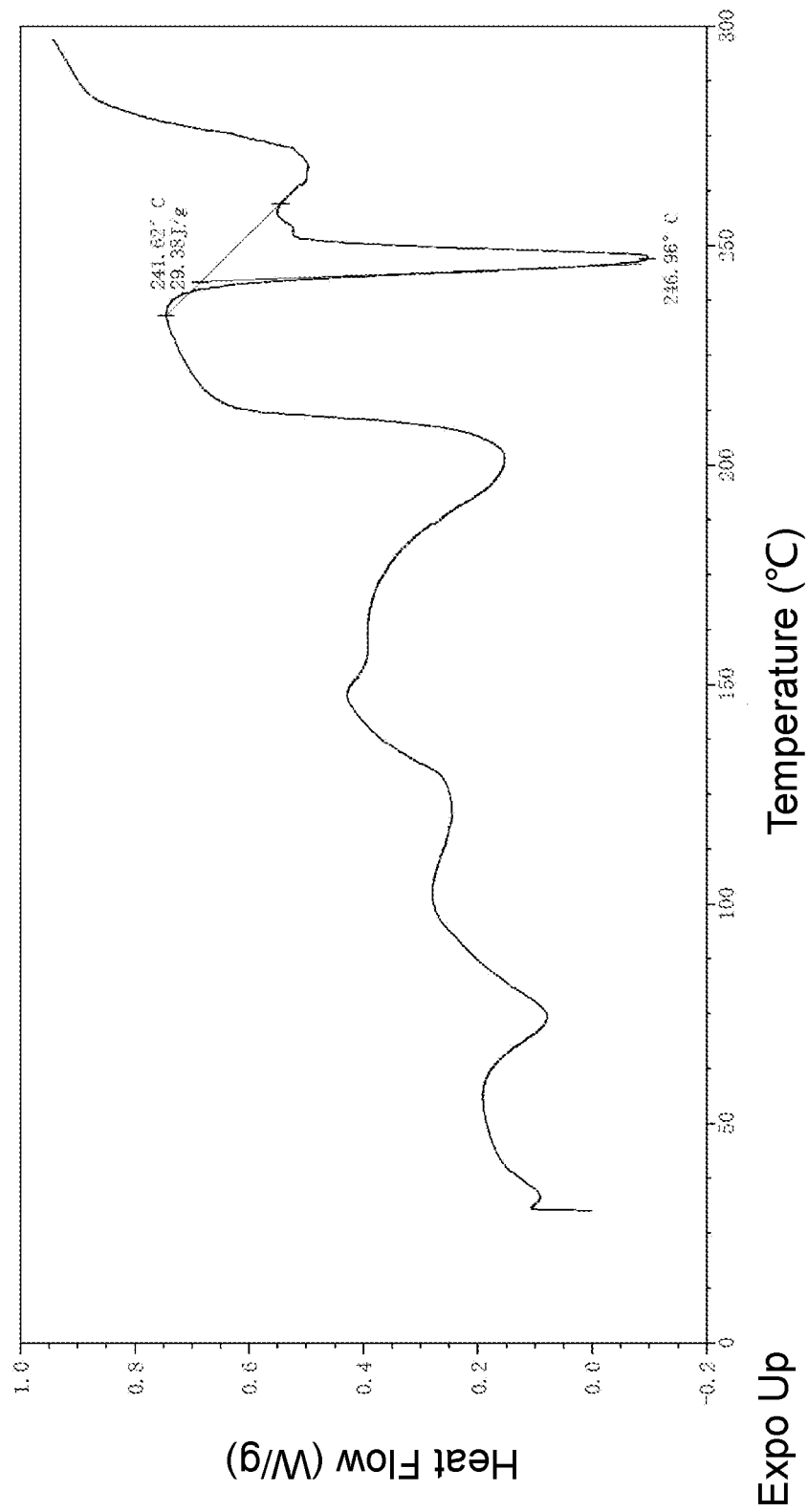
FIG. 22 is a DSC plot of 6-Acetyl-8-cyclopentyl-5-methyl-2-(5-piperazin-1-yl-pyridin-2-ylamino)-8H-pyrido

A differential scanning calorimetry (DSC) analysis was performed on the crystal Form X in Example 10, using a TA Q2000 differential scanning calorimeter using an N₂ atmosphere at a temperature rising rate of 10° C./min. The DSC plot of Form X is shown in FIG. 22.

The thermogravimetric (TGA) analysis of the crystal Form X in Example 10 was carried out using a TA Q500 thermogravimetric analyzer using a N₂ atmosphere at a heating rate of 10° C./min. The TGA plot of Form X is shown in FIG. 33.

Example 11

Twenty (20) mg of 6-Acetyl-8-cyclopentyl-5-methyl-2-(5-piperazin-1-yl-pyridin-2-ylamino)-8H-pyrido[2,3-d]pyrimidin-7-one was dissolved in 0.5 mL of acetic acid and then methanol was added drop wise until the solution became turbid. The crystal Form XI was obtained after the filtration.

Figure 11:
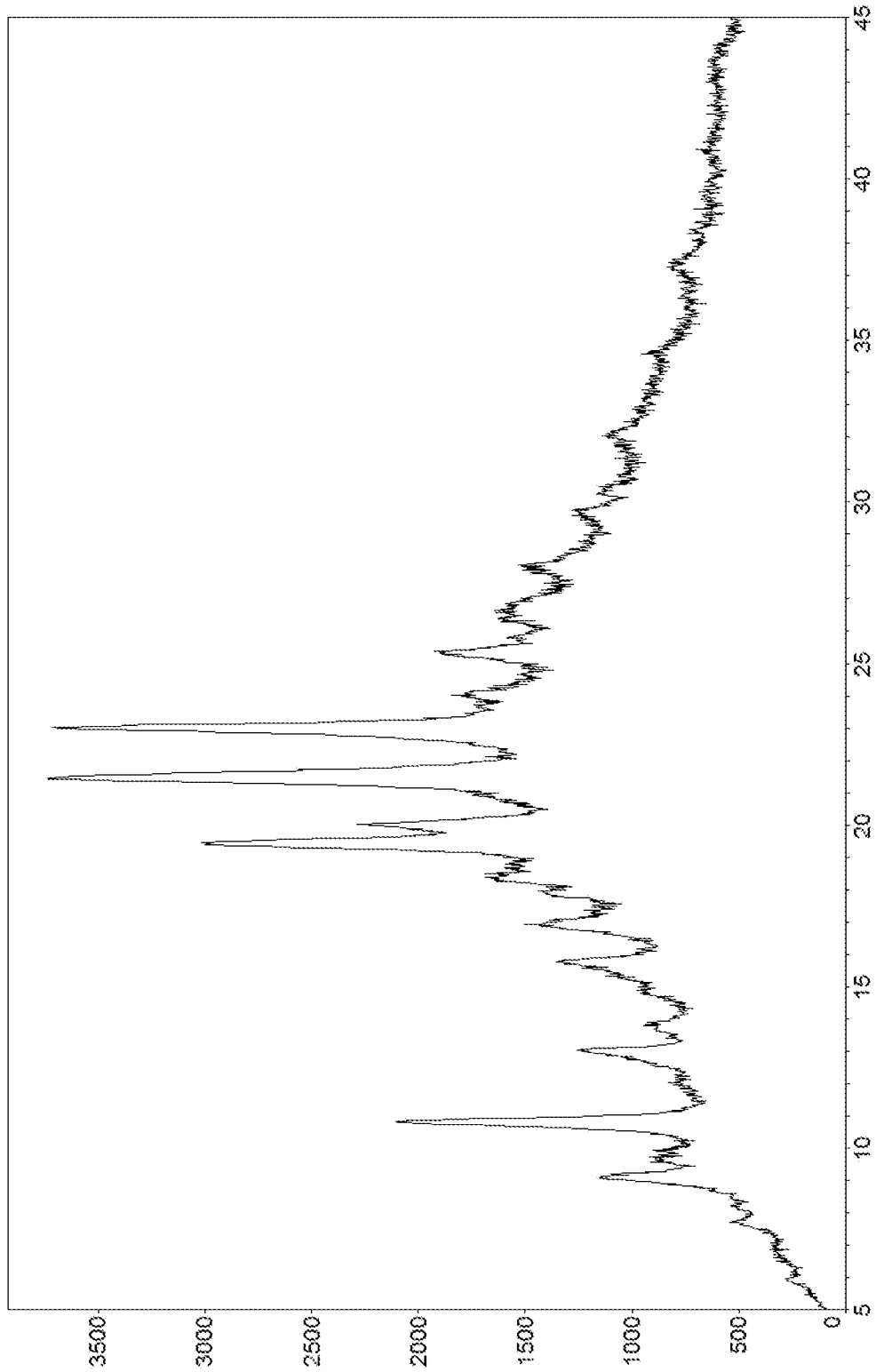
FIG. 11 is an XRPD pattern of 6-Acetyl-8-cyclopentyl-5-methyl-2-(5-piperazin-1-yl-pyridin-2-ylamino)-8H-pyrido[2,3-d]pyrimidin-7-one Form XI. 2θ values in unit of degree in accordance with the abscissa. The intensity of diffraction peak as ordinate.

The XRPD pattern of the resulting crystal Form XI is shown in FIG. 11 and information of diffraction peaks at 2θ values was list in the following table:

| 2θ (degree) | d (Å) | I (Height) % |
|---|---|---|
| 9.119 | 9.6894 | 21.6 |
| 10.84 | 8.1546 | 62.9 |
| 13.059 | 6.7739 | 21.9 |
| 15.781 | 5.6112 | 20.1 |
| 16.941 | 5.2294 | 22.5 |
| 18.399 | 4.8182 | 14.6 |
| 19.46 | 4.5578 | 68.9 |
| 20.04 | 4.4272 | 36.6 |
| 21.46 | 4.1373 | 100 |
| 23.02 | 3.8603 | 94.9 |
| 25.379 | 3.5066 | 21.7 |

A differential scanning calorimetry (DSC) analysis was performed on the crystal Form XI in Example 11, using a TA Q2000 differential scanning calorimeter using an N₂ atmosphere at a temperature rising rate of 10° C./min. The DSC plot of Form XI is shown in FIG. 23.

The thermogravimetric (TGA) analysis of the crystal Form XI in Example 11 was carried out using a TA Q500 thermogravimetric analyzer using a N₂ atmosphere at a heating rate of 10° C./min. The TGA plot of Form XI is shown in FIG. 34.

Example 12

Twenty (20) mg of 6-Acetyl-8-cyclopentyl-5-methyl-2-(5-piperazin-1-yl-pyridin-2-ylamino)-8H-pyrido[2,3-d]pyrimidin-7-one was dissolved in 0.5 mL of trifluoroethanol and then the solution was rapidly added into 10 mL of N-butanol to yield precipitation. The crystal Form XII was obtained after filtration.

Figure 12:
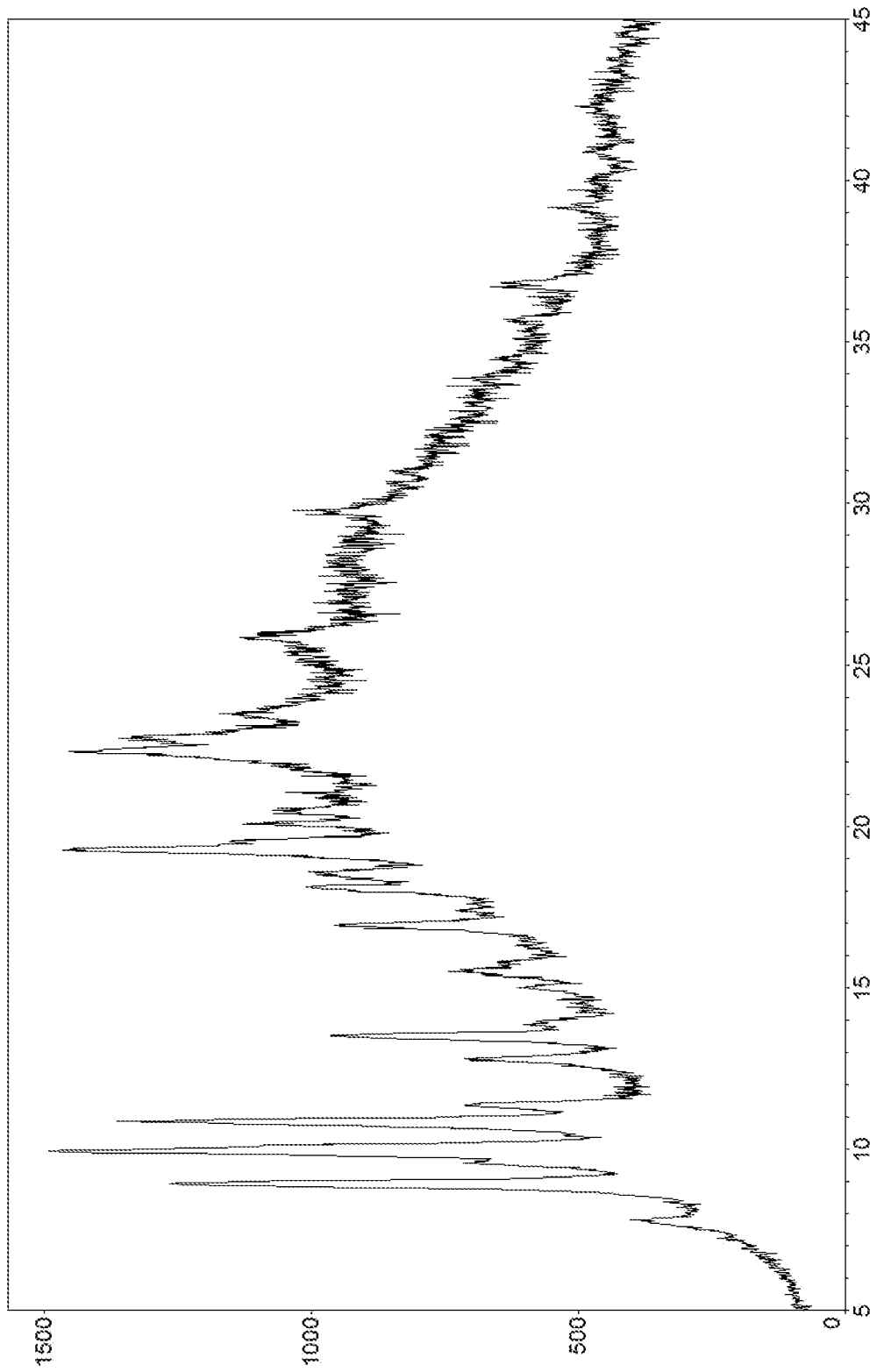
FIG. 12 is an XRPD pattern of 6-Acetyl-8-cyclopentyl-5-methyl-2-(5-piperazin-1-yl-pyridin-2-ylamino)-8H-pyrido[2,3-d]pyrimidin-7-one Form XII. 2θ values in unit of degree in accordance with the abscissa. The intensity of diffraction peak as ordinate.
Figure 13:
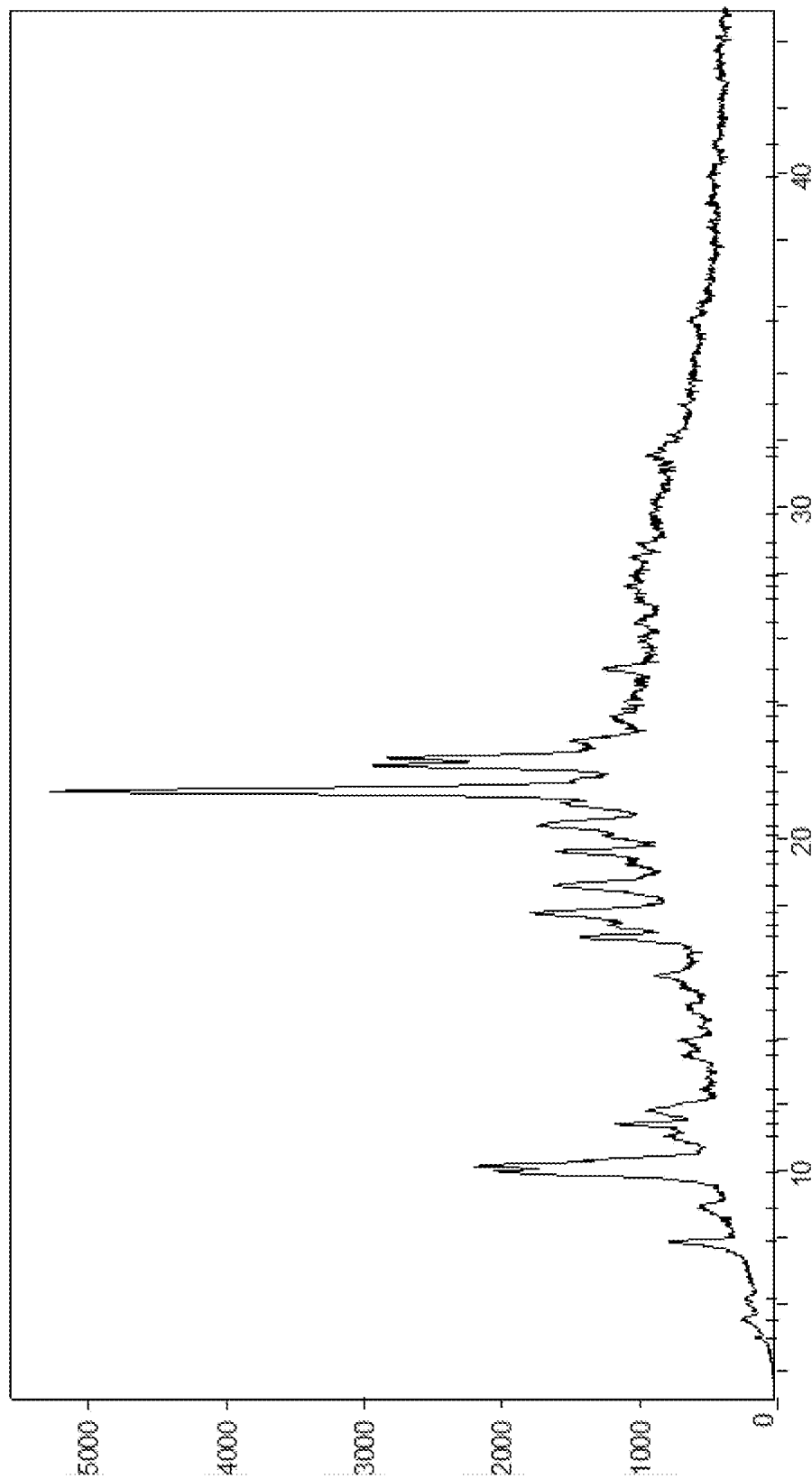
FIG. 13 is an XRPD pattern of 6-Acetyl-8-cyclopentyl-5-methyl-2-(5-piperazin-1-yl-pyridin-2-ylamino)-8H-pyrido[2,3-d]pyrimidin-7-one Form XIV. 2θ values in unit of degree in accordance with the abscissa. The intensity of diffraction peak as ordinate.

The XRPD pattern of the resulting crystal Form XII is shown in FIG. 12 and information of diffraction peaks at 2θ values was listed in the following table:

| 2θ (degree) | d (Å) | I (Height) % |
|---|---|---|
| 7.819 | 11.2981 | 14.9 |
| 8.96 | 9.8619 | 85 |
| 9.582 | 9.223 | 26.4 |
| 9.959 | 8.8741 | 100 |
| 10.88 | 8.1248 | 88.8 |
| 11.399 | 7.7563 | 27.8 |
| 12.819 | 6.9002 | 26.7 |
| 13.538 | 6.535 | 49.5 |
| 15.02 | 5.8937 | 8.8 |
| 15.501 | 5.7116 | 19.8 |
| 16.958 | 5.224 | 30.9 |
| 18.14 | 4.8864 | 23.9 |
| 18.596 | 4.7675 | 19 |
| 19.262 | 4.6041 | 59.5 |
| 20.08 | 4.4184 | 22.6 |
| 20.498 | 4.3291 | 16.9 |
| 22.32 | 3.9798 | 46.4 |
| 22.721 | 3.9105 | 31.2 |

A differential scanning calorimetry (DSC) analysis was performed on the crystal Form XII in Example 12, using a TA Q2000 differential scanning calorimeter using an N₂ atmosphere at a temperature rising rate of 10° C./min. The DSC plot of Form XII is shown in FIG. 24.

The thermogravimetric (TGA) analysis of the crystal Form XII in Example 12 was carried out using a TA Q500 thermogravimetric analyzer using a N₂ atmosphere at a heating rate of 10° C./min. The TGA plot of Form XII is shown in FIG. 35.

Example 13

The obtained crystal Form IX was placed into an aluminum pan for DSC and then heated to 269° C. under N₂ atmosphere to yield crystal Form XIV of 6-Acetyl-8-cyclopentyl-5-methyl-2-(5-piperazin-1-yl-pyridin-2-ylamino)-8H-pyrido[2,3-d]pyrimidin-7-one.

| 2θ (degree) | d (Å) | I (Height) % |
|---|---|---|
| 7.819 | 11.2981 | 14.9 |
| 8.96 | 9.8619 | 85 |
| 9.582 | 9.223 | 26.4 |
| 9.959 | 8.8741 | 100 |
| 10.88 | 8.1248 | 88.8 |
| 11.399 | 7.7563 | 27.8 |
| 12.819 | 6.9002 | 26.7 |
| 13.538 | 6.535 | 49.5 |
| 15.02 | 5.8937 | 8.8 |
| 15.501 | 5.7116 | 19.8 |
| 16.958 | 5.224 | 30.9 |
| 18.14 | 4.8864 | 23.9 |
| 18.596 | 4.7675 | 19 |
| 19.262 | 4.6041 | 59.5 |
| 20.08 | 4.4184 | 22.6 |
| 20.498 | 4.3291 | 16.9 |

-continued

| 2θ (degree) | d (Å) | I (Height) % |
|---|---|---|
| 22.32 | 3.9798 | 46.4 |
| 22.721 | 3.9105 | 31.2 |

Example 14

The solubility of several new crystal Forms prepared in the above examples and Form A and B (prepared according to the method of WO2014128588A1) in a pH buffer solution (pH 6.8) was determined. 20 mg Form VIII, Form IX, Form XIV, Form A and Form B was precisely weighed and placed in a 2-mL glass vial, 1 mL of pH 6.8 buffer was added, sealed with cap, and mixed on a rotating mixer. After the suspension was equilibrated for 1 hour, the mixture was filtered through a 0.45 μm needle filter, and the concentration of 6-Acetyl-8-cyclopentyl-5-methyl-2-(5-piperazin-1-yl-pyridin-2-ylamino)-8H-pyrido[2,3-d]pyrimidin-7-one in the filtrate was analyzed by HPLC to obtain the solubility of different crystal Forms. The solubility of the polymorphs of 6-Acetyl-8-cyclopentyl-5-methyl-2-(5-piperazin-1-yl-pyridin-2-ylamino)-8H-pyrido[2,3-d]pyrimidin-7-one is shown in the following table:

| | Crystal forms | | | | |
|---|---|---|---|---|---|
| | Form VIII | Form IX | Form XIV | Form A | Form B |
| Solubility in pH 6.8 buffer (mg/mL) | 0.010 | 0.015 | 0.012 | 0.002 | 0.003 |

What is claimed is:

1. A crystal form VIII of 6-Acetyl-8-cyclopentyl-5-methyl-2-(5-piperazin-1-yl-pyridin-2-ylamino)-8H-pyrido[2,3-d]pyrimidin-7-one, wherein an X-ray powder diffraction pattern of the crystal form VIII includes diffraction peaks at least one 2θ value of 10.3±0.2, 10.0±0.2, 21.6±0.2, 12.0±0.2, or 20.5±0.2.

2. The crystal form VIII of claim 1, wherein the diffraction peaks are measured using CuKα radiation.

3. The crystal form VIII of claim 1, wherein the X-ray powder diffraction pattern further includes diffraction peaks at least one 2θ value of 20.9±0.2, 17.5±0.2, 14.0±0.2, 18.9±0.2, or 31.6±0.2.

4. The crystal form VIII of claim 1, wherein the X-ray powder diffraction pattern further includes diffraction peaks at least one 2θ value of 7.8±0.2, 22.5±0.2, 18.6±0.2, 15.6±0.2, or 5.2±0.2.

* * * * *